(12) United States Patent
Tanaka et al.

(10) Patent No.: US 7,811,274 B2
(45) Date of Patent: *Oct. 12, 2010

(54) METHOD FOR TREATING CHRONIC OBSTRUCTIVE PULMONARY DISEASE

(75) Inventors: Don Tanaka, Saratoga, CA (US); Scott M. Russell, San Jose, CA (US)

(73) Assignee: Portaero, Inc., Cupertino, CA (US)

( * ) Notice: Subject to any disclaimer, the term of this patent is extended or adjusted under 35 U.S.C. 154(b) by 1007 days.

This patent is subject to a terminal disclaimer.

(21) Appl. No.: 10/832,905

(22) Filed: Apr. 27, 2004

(65) Prior Publication Data

US 2004/0225254 A1    Nov. 11, 2004

Related U.S. Application Data

(60) Provisional application No. 60/468,415, filed on May 7, 2003.

(51) Int. Cl.
*A61M 31/00* (2006.01)
(52) U.S. Cl. .......... 604/502; 604/523; 604/506
(58) Field of Classification Search ............. 604/523, 604/53, 158, 280, 656
See application file for complete search history.

(56) References Cited

U.S. PATENT DOCUMENTS

| | | | |
|---|---|---|---|
| 733,152 A * | 7/1903 | Chisholm | 604/247 |
| 953,922 A | 4/1910 | Rogers | |
| 2,206,687 A | 7/1940 | Bloomheart | |
| 2,867,213 A | 1/1959 | Thomas, Jr. | |
| 2,873,742 A | 2/1959 | Shelden | |
| 2,991,787 A | 7/1961 | Shelden et al. | |
| 3,253,594 A | 5/1966 | Matthews et al. | |
| 3,384,087 A | 5/1968 | Brummelkamp | |
| 3,463,159 A | 8/1969 | Heimlich | |
| 3,511,243 A | 5/1970 | Toy | |
| 3,556,103 A | 1/1971 | Calhoun et al. | |
| 3,638,649 A | 2/1972 | Ersek | |
| 3,682,166 A | 8/1972 | Jacobs | |
| 3,688,773 A | 9/1972 | Weiss | |

(Continued)

FOREIGN PATENT DOCUMENTS

EP    0260543 A1    3/1988

(Continued)

OTHER PUBLICATIONS

European Search Report dated Aug. 31, 2004 for corresponding Appln. No. 04 25 2638.

(Continued)

*Primary Examiner*—Kevin C Sirmons
*Assistant Examiner*—Phillip Gray
(74) *Attorney, Agent, or Firm*—Fliesler Meyer LLP

(57) ABSTRACT

A ventilation bypass system which alleviates symptoms of chronic obstructive pulmonary disease by allowing air to exit the lung of a patient through the thoracic wall bypassing the natural airways. A pleurodesis is formed between the visceral and parietal membranes surrounding a lung and an opening is made through the thoracic wall into the lung via the pleurodesis. The ventilation bypass system includes a conduit placed through the opening in the thoracic wall into the lung, a flange for securing the conduit to the thoracic wall and preventing over-insertion of the conduit, and a flow control device for controlling flow of material out of the lung.

45 Claims, 6 Drawing Sheets

U.S. PATENT DOCUMENTS

| | | | |
|---|---|---|---|
| 3,777,757 A | 12/1973 | Gray et al. | |
| 3,788,326 A | 1/1974 | Jacobs | |
| 3,817,250 A | 6/1974 | Weiss et al. | |
| 3,908,704 A | 9/1975 | Clement et al. | |
| 3,916,903 A | 11/1975 | Pozzi | |
| 4,153,058 A * | 5/1979 | Nehme | 604/247 |
| 4,291,694 A | 9/1981 | Chai | |
| 4,439,189 A | 3/1984 | Sargeant et al. | |
| 4,465,062 A | 8/1984 | Versaggi et al. | |
| 4,502,482 A | 3/1985 | DeLuccia et al. | |
| 4,583,977 A | 4/1986 | Shishov et al. | |
| 4,664,660 A | 5/1987 | Goldberg et al. | |
| 4,799,494 A | 1/1989 | Wang | |
| 4,813,929 A | 3/1989 | Semrad | |
| 4,826,495 A | 5/1989 | Petersen | |
| 4,828,553 A | 5/1989 | Nielsen | |
| 4,869,717 A | 9/1989 | Adair | |
| 4,872,869 A | 10/1989 | Johns | |
| 4,889,534 A | 12/1989 | Mohiuddin et al. | |
| 4,931,045 A | 6/1990 | Steer | |
| 4,944,724 A | 7/1990 | Goldberg et al. | |
| 4,959,054 A | 9/1990 | Heimke et al. | |
| 4,976,688 A | 12/1990 | Rosenblum | |
| 5,004,456 A * | 4/1991 | Botterbusch et al. | 604/512 |
| 5,060,645 A | 10/1991 | Russell | |
| 5,078,689 A | 1/1992 | Keller | |
| 5,137,509 A | 8/1992 | Freitas | |
| 5,139,485 A | 8/1992 | Smith et al. | |
| 5,218,957 A | 6/1993 | Strickland | |
| 5,230,332 A | 7/1993 | Strickland | |
| 5,230,350 A | 7/1993 | Fentress | |
| 5,261,708 A | 11/1993 | Steer | |
| 5,263,939 A | 11/1993 | Wortrich | |
| 5,312,331 A | 5/1994 | Knoepfler | |
| 5,315,992 A | 5/1994 | Dalton | |
| 5,336,206 A | 8/1994 | Shichman | |
| 5,354,283 A | 10/1994 | Bark et al. | |
| 5,356,386 A | 10/1994 | Goldberg et al. | |
| 5,366,478 A * | 11/1994 | Brinkerhoff et al. | 606/213 |
| 5,370,625 A | 12/1994 | Shichman | |
| 5,376,376 A | 12/1994 | Li | |
| 5,389,077 A | 2/1995 | Melinyshyn et al. | |
| 5,401,262 A | 3/1995 | Karwoski et al. | |
| 5,431,633 A | 7/1995 | Fury | |
| 5,478,333 A | 12/1995 | Asherman, Jr. | |
| 5,484,401 A | 1/1996 | Rodriguez et al. | |
| 5,496,297 A | 3/1996 | Olsen | |
| 5,501,677 A | 3/1996 | Jensen | |
| 5,501,678 A | 3/1996 | Olsen | |
| 5,588,424 A | 12/1996 | Insler et al. | |
| 5,616,131 A | 4/1997 | Sauer et al. | |
| 5,660,175 A | 8/1997 | Dayal | |
| 5,662,629 A | 9/1997 | Steer et al. | |
| 5,728,066 A | 3/1998 | Daneshvar | |
| 5,730,735 A | 3/1998 | Holmberg et al. | |
| 5,738,661 A | 4/1998 | Larice | |
| 5,741,248 A * | 4/1998 | Stern et al. | 606/21 |
| 5,807,341 A | 9/1998 | Heim | |
| 5,830,200 A | 11/1998 | Steer et al. | |
| 5,843,053 A | 12/1998 | Steer | |
| 5,897,531 A * | 4/1999 | Amirana | 604/180 |
| 5,931,821 A | 8/1999 | Weilbacher et al. | |
| 5,954,636 A | 9/1999 | Schwartz et al. | |
| 5,971,962 A | 10/1999 | Kojima et al. | |
| 5,972,026 A | 10/1999 | Laufer et al. | |
| 6,059,816 A | 5/2000 | Moenning | |
| 6,083,255 A | 7/2000 | Laufer et al. | |
| 6,174,323 B1 | 1/2001 | Biggs et al. | |
| 6,197,010 B1 | 3/2001 | Leise, Jr. et al. | |
| 6,200,333 B1 | 3/2001 | Laufer | |
| 6,258,100 B1 | 7/2001 | Alferness et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,287,290 B1 | 9/2001 | Perkins et al. | |
| 6,293,930 B1 | 9/2001 | Brunsgaard et al. | |
| 6,293,951 B1 | 9/2001 | Alferness et al. | |
| 6,299,633 B1 | 10/2001 | Laufer | |
| 6,322,536 B1 | 11/2001 | Rosengart et al. | |
| 6,328,689 B1 | 12/2001 | Gonzalez et al. | |
| 6,330,882 B1 | 12/2001 | French | |
| 6,334,441 B1 | 1/2002 | Zowtiak et al. | |
| 6,358,269 B1 | 3/2002 | Aye | |
| 6,398,775 B1 | 6/2002 | Perkins et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,432,100 B1 | 8/2002 | Affeld | |
| 6,443,156 B1 | 9/2002 | Niklason et al. | |
| 6,468,292 B1 | 10/2002 | Mollenauer et al. | |
| 6,485,407 B2 | 11/2002 | Alferness et al. | |
| 6,488,673 B1 | 12/2002 | Laufer et al. | |
| 6,491,706 B1 | 12/2002 | Alferness et al. | |
| 6,514,290 B1 | 2/2003 | Loomas | |
| 6,517,519 B1 | 2/2003 | Rosen et al. | |
| 6,520,183 B2 | 2/2003 | Amar | |
| 6,527,761 B1 | 3/2003 | Soltesz et al. | |
| 6,550,475 B1 | 4/2003 | Oldfield | |
| 6,569,121 B1 | 5/2003 | Purow et al. | |
| 6,569,166 B2 | 5/2003 | Gonzalez | |
| 6,585,639 B1 | 7/2003 | Kotmel et al. | |
| 6,589,161 B2 | 7/2003 | Corcoran | |
| 6,592,594 B2 | 7/2003 | Rimbaugh et al. | |
| 6,599,311 B1 | 7/2003 | Biggs et al. | |
| 6,609,521 B1 | 8/2003 | Belani et al. | |
| 6,629,951 B2 | 10/2003 | Laufer et al. | |
| 6,632,239 B2 | 10/2003 | Snyder et al. | |
| 6,632,243 B1 | 10/2003 | Zadno-Azizi et al. | |
| 6,634,360 B1 | 10/2003 | Flodin | |
| 6,634,363 B1 | 10/2003 | Laufer et al. | |
| 6,638,253 B2 | 10/2003 | Breznock | |
| 6,653,525 B2 | 11/2003 | Ingenito et al. | |
| 6,659,961 B2 | 12/2003 | Robinson | |
| 6,679,264 B1 | 1/2004 | Deem et al. | |
| 6,682,506 B1 | 1/2004 | Navarro | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,712,812 B2 | 3/2004 | Roschak et al. | |
| 6,736,797 B1 | 5/2004 | Larsen et al. | |
| 6,749,606 B2 | 6/2004 | Keast et al. | |
| 6,770,063 B2 | 8/2004 | Goldberg et al. | |
| 6,770,070 B1 | 8/2004 | Balbierz | |
| 6,790,172 B2 | 9/2004 | Alferness et al. | |
| 6,827,086 B2 | 12/2004 | Shuman | |
| 6,837,906 B2 | 1/2005 | Ginn | |
| 6,840,243 B2 | 1/2005 | Deem et al. | |
| 6,843,767 B2 | 1/2005 | Corcoran et al. | |
| 6,846,292 B2 | 1/2005 | Bakry | |
| 6,849,061 B2 | 2/2005 | Wagner | |
| 6,852,108 B2 | 2/2005 | Barry et al. | |
| 6,860,847 B2 | 3/2005 | Alferness et al. | |
| 6,878,141 B1 | 4/2005 | Perkins et al. | |
| 6,886,558 B2 | 5/2005 | Tanaka | |
| 6,901,927 B2 | 6/2005 | Deem et al. | |
| 6,904,909 B2 | 6/2005 | Andreas et al. | |
| 6,905,518 B2 | 6/2005 | Ginn | |
| 6,916,310 B2 | 7/2005 | Sommerich | |
| 6,929,637 B2 | 8/2005 | Gonzalez et al. | |
| 6,941,950 B2 | 9/2005 | Wilson et al. | |
| 6,997,189 B2 | 2/2006 | Biggs et al. | |
| 6,997,918 B2 | 2/2006 | Soltesz et al. | |
| 7,011,094 B2 | 3/2006 | Rapacki et al. | |

| Patent/Pub No. | Date | Inventor |
|---|---|---|
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,086,398 B2 | 8/2006 | Tanaka |
| 7,100,616 B2 | 9/2006 | Springmeyer |
| 7,135,010 B2 | 11/2006 | Buckman et al. |
| 7,141,046 B2 | 11/2006 | Perkins et al. |
| 7,165,548 B2 | 1/2007 | Deem et al. |
| 7,172,581 B2 | 2/2007 | Ciok et al. |
| 7,175,644 B2 | 2/2007 | Cooper et al. |
| 7,182,772 B2 | 2/2007 | Alferness et al. |
| 7,186,259 B2 | 3/2007 | Perkins et al. |
| 7,192,420 B2 | 3/2007 | Whiteford |
| 7,195,016 B2 | 3/2007 | Loyd et al. |
| 7,195,017 B2 | 3/2007 | Tanaka |
| 7,207,946 B2 | 4/2007 | Sirokman |
| 7,232,414 B2 | 6/2007 | Gonzalez |
| 7,244,245 B2 | 7/2007 | Purow et al. |
| 7,252,086 B2 | 8/2007 | Tanaka |
| 7,533,667 B2 * | 5/2009 | Tanaka ................ 128/200.24 |
| 2001/0025132 A1 | 9/2001 | Alferness et al. |
| 2001/0041906 A1 | 11/2001 | Gonzalez |
| 2001/0041932 A1 | 11/2001 | Scholz et al. |
| 2002/0042564 A1 | 4/2002 | Cooper et al. |
| 2002/0062120 A1 | 5/2002 | Perkins et al. |
| 2002/0077593 A1 | 6/2002 | Perkins et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0165618 A1 | 11/2002 | Ingenito et al. |
| 2002/0188171 A1 | 12/2002 | Alferness et al. |
| 2003/0013935 A1 | 1/2003 | Alferness et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0065339 A1 | 4/2003 | Snyder et al. |
| 2003/0069488 A1 | 4/2003 | Alferness et al. |
| 2003/0078469 A1 | 4/2003 | Corcoran |
| 2003/0083542 A1 | 5/2003 | Alferness et al. |
| 2003/0083671 A1 | 5/2003 | Rimbaugh et al. |
| 2003/0127090 A1 | 7/2003 | Gifford et al. |
| 2003/0130593 A1 | 7/2003 | Gonzalez |
| 2003/0149446 A1 | 8/2003 | Shuman |
| 2003/0154988 A1 | 8/2003 | DeVore et al. |
| 2003/0158515 A1 | 8/2003 | Gonzalez et al. |
| 2003/0163024 A1 | 8/2003 | Corcoran |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0186904 A1 | 10/2003 | Ruben et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0216730 A1 | 11/2003 | Barry et al. |
| 2003/0216769 A1 | 11/2003 | Dillard et al. |
| 2003/0228344 A1 | 12/2003 | Fields et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0016435 A1 | 1/2004 | Deem et al. |
| 2004/0024356 A1 | 2/2004 | Tanaka |
| 2004/0031494 A1 | 2/2004 | Danek et al. |
| 2004/0040555 A1 | 3/2004 | Tanaka |
| 2004/0047855 A1 | 3/2004 | Ingenito |
| 2004/0055606 A1 | 3/2004 | Hendricksen et al. |
| 2004/0059263 A1 | 3/2004 | DeVore et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078026 A1 | 4/2004 | Wagner |
| 2004/0078054 A1 | 4/2004 | Biggs et al. |
| 2004/0097983 A1 | 5/2004 | Snyder et al. |
| 2004/0143282 A1 | 7/2004 | Dillard et al. |
| 2004/0144387 A1 | 7/2004 | Amar |
| 2004/0158228 A1 | 8/2004 | Perkins et al. |
| 2004/0167636 A1 | 8/2004 | Dillard et al. |
| 2004/0173218 A1 | 9/2004 | Yamada et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0220446 A1 | 11/2004 | Corcoran et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0237966 A1 | 12/2004 | Tanaka |
| 2004/0243140 A1 | 12/2004 | Alferness et al. |
| 2004/0244802 A1 | 12/2004 | Tanaka |
| 2004/0244803 A1 | 12/2004 | Tanaka |
| 2005/0005936 A1 | 1/2005 | Wondka |
| 2005/0015106 A1 | 1/2005 | Perkins et al. |
| 2005/0022809 A1 | 2/2005 | Wondka |
| 2005/0025816 A1 | 2/2005 | Tanaka |
| 2005/0033310 A1 | 2/2005 | Alferness et al. |
| 2005/0033344 A1 | 2/2005 | Dillard et al. |
| 2005/0043745 A1 | 2/2005 | Alferness et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0066976 A1 | 3/2005 | Wondka |
| 2005/0085801 A1 | 4/2005 | Cooper et al. |
| 2005/0096529 A1 | 5/2005 | Cooper et al. |
| 2005/0103340 A1 | 5/2005 | Wondka |
| 2005/0107783 A1 | 5/2005 | Tom et al. |
| 2005/0131276 A1 | 6/2005 | Alferness et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca' et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle, Jr. |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |
| 2006/0076023 A1 | 4/2006 | Rapacki et al. |
| 2006/0079838 A1 | 4/2006 | Walker et al. |
| 2006/0095002 A1 | 5/2006 | Soltesz et al. |

| | | | |
|---|---|---|---|
| 2006/0107961 A1 | 5/2006 | Tanaka | |
| 2006/0116749 A1 | 6/2006 | Willink et al. | |
| 2006/0118125 A1 | 6/2006 | Tanaka | |
| 2006/0118126 A1 | 6/2006 | Tanaka | |
| 2006/0124126 A1 | 6/2006 | Tanaka | |
| 2006/0130830 A1 | 6/2006 | Barry | |
| 2006/0135947 A1 | 6/2006 | Soltesz et al. | |
| 2006/0135984 A1 | 6/2006 | Kramer et al. | |
| 2006/0142672 A1 | 6/2006 | Keast et al. | |
| 2006/0161233 A1 | 7/2006 | Barry et al. | |
| 2006/0162731 A1 | 7/2006 | Wondka et al. | |
| 2006/0206147 A1 | 9/2006 | DeVore et al. | |
| 2006/0212046 A1 | 9/2006 | Pearce et al. | |
| 2006/0212051 A1 | 9/2006 | Snyder et al. | |
| 2006/0235432 A1 | 10/2006 | DeVore et al. | |
| 2006/0235467 A1 | 10/2006 | DeVore | |
| 2006/0264772 A1 | 11/2006 | Aljuri et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2006/0283462 A1 | 12/2006 | Fields et al. | |
| 2007/0005083 A1 | 1/2007 | Sabanathan et al. | |
| 2007/0027434 A1 | 2/2007 | Pedersen et al. | |
| 2007/0043350 A1 | 2/2007 | Soltesz et al. | |
| 2007/0051372 A1 | 3/2007 | Tanaka | |
| 2007/0055175 A1 | 3/2007 | Caro | |
| 2007/0088300 A1 | 4/2007 | Cline et al. | |
| 2007/0123922 A1 | 5/2007 | Cooper et al. | |
| 2007/0128174 A1 | 6/2007 | Kleinsek et al. | |
| 2007/0142742 A1 | 6/2007 | Aljuri et al. | |
| 2007/0163598 A1 | 7/2007 | Chang et al. | |
| 2007/0185531 A1 | 8/2007 | Rimbaugh et al. | |
| 2007/0186932 A1 | 8/2007 | Wondka et al. | |
| 2007/0186933 A1 | 8/2007 | Domingo et al. | |

FOREIGN PATENT DOCUMENTS

| | | |
|---|---|---|
| EP | 0609950 A1 | 8/1994 |
| EP | 0609950 A1 | 10/1994 |
| EP | 1393760 A1 | 3/2004 |
| RU | 2192185 | 10/2002 |
| WO | WO 88/01879 | 3/1988 |
| WO | WO 90/04982 | 5/1990 |
| WO | WO 99/45990 | 9/1999 |
| WO | WO 99/66975 | 12/1999 |
| WO | WO 00/76577 A1 | 12/2000 |
| WO | WO 01/02042 A1 | 1/2001 |
| WO | WO 01/45568 A1 | 6/2001 |
| WO | WO 02/076279 A2 | 10/2002 |
| WO | WO 02/096325 A1 | 12/2002 |
| WO | WO 03/007821 A1 | 1/2003 |
| WO | WO 03/020338 A2 | 3/2003 |
| WO | WO 03/061480 A1 | 7/2003 |

OTHER PUBLICATIONS

Al-Salem et al., "Computed tomography-guided percutaneous needle aspiration of lung abscesses in neonates and children", Pediatr Surg Int (1997) 12: 417-419, copyright Springer-Verlag 1997.
Ball, JR et al., "Percutaneous Drainage of Chest Abscesses in Children", Radiology 1989; 171: 431-434.
Becker et al., "Lung Volumes before and after Lung Volume Reduction Surgery: Quantitative CT Analysis", Am J Respir Crit Care Med 1998; 157: 1593-1599.
Brenner et al., "Innovative Approaches to Lung Volume Reduction for Emphysema", Chest 2004; 126: 238-248.
Brutinel et al., "A two-year experience with the neodymium-YAG laser in endobronchial obstruction", Chest 1987; 91: 159-165.
Celli et al. "Standards for the diagnosis and treatment of patients with COPD: a summary of the ATS/ERS position paper", European Respiratory Journal 2004; 23; 932-946.
Cetti et al., "Collateral ventilation", Thorax 2006; 61: 371-373.
Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System.
Choong et al., "Feasibility and safety of airway bypass stent placement and influence of topical mitomycin C on stent patency", The Journal of Thoracic and Cardiovascular Surgery 2005; 129: 632-638.
Choong et al., "Transpleural ventilation of explanted human lungs", Thorax 2007; 62: 623-630; originally published online Apr. 5, 2007.
Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.
Dumon, J. F., "A Dedicated Tracheobronchial Stent", Chest 1990; 97: 328-332.
Fein, Alan M, "Lung Volume Reduction Surgery: Answering the Crucial Questions", Chest 1998; 113: 277-282.
Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.
Fessler, Henry E., "Collateral Ventilation, the Bane of Bronchoscopic Volume Reduction", Am J Respir Crit Care Med 2005; 171: 423-425.
Frawley et al., "Airway Pressure Release Ventilation: Theory and Practice", AACN Clinical Issues 2001; vol. 12, No. 2: 234-246.
Freitag et al., "Theoretical and experimental basis for the development of a dynamic airway stent", European Respiratory Journal 1994; 7: 2038-2045.
Ghaye et al., "Imaging guided thoracic interventions", European Respiratory Journal 2001; 17: 507-528.
Golding et al., "External drainage of large bullae in severe generalized emphysema", Journal of Thoracic and Cardiovascular Surgery Jun. 1968; vol. 55, No. 6: 891-894.
Goldstraw et al., "The Surgical Treatment of Emphysema: The Brompton Approach", Chest Surgery Clinics of North America Nov. 1995; vol. 5, No. 4: 777-797.
Habashi, Nader M., "Other approaches to open-lung ventilation: Airway pressure release ventilation", Crit Care Med 2005, vol. 33, No. 3 (Suppl): S228-S240.
Harada et al., "Re-expansion of Refractory Atelectasis Using a Bronchofberscope with a Balloon Cuff", Chest 1983; 84: 725-728.
Head et al.; "Intracavitary Suction (Monaldi) in the Treatment of Emphysematous Bullae and Blebs", Journal of Thoracic Surgery Dec. 1949; vol. 18, No. 6: 761-776.
Heimlich, Henry J., "Respiratory Rehabilitation with Transtracheal Oxygen System", Ann Otol Rhinol Laryngol Nov./Dec. 1982; 91: 643-647.
Hogg et al., "Chronic obstructive pulmonary disease c2: Pathology and biochemistry of emphysema", Thorax 2002; 57: 830-834.
Joannette, Albert, "Drainage of Tuberculous Cavities by Aspiration (Monaldi Method)", The Canadian Medical Association Journal Jan. 1941; 46-48.
Korpela et al., "Bioabsorbable Self-reinforced Poly-L-Lactide, Metallic, and Silicone Stents in the Management of Experimental Tracheal Stenosis", Chest 1999; 115: 490-495.
Lausberg et al., "Bronchial Fenestration Improves Expiratory Flow in Emphysematous Human Lungs", Annals of Thoracic Surgery 2003; 75: 393-398.
Lorenzo et al., "Lung Abscesses in Children: Diagnostic and Therapeutic Needle Aspiration", Radiology Oct. 1985; 157: 79-80.
MacArthur et al., "Intracavity suction and drainage in the treatment of emphysematous bullae", Thorax 1977; 32: 668-672.
MacKlem, Peter T., "Collateral Ventilation", The New England Journal of Medicine Jan. 5, 1978; 298(1): 49-50.
Matson et al., "Evaluation of Various Surgical Procedures in the Treatment of Pulmonary Tuberculosis", Chest 1946; 12: 40-47.
McCoy, Robert, "Oxygen-Conserving Techniques and Devices", Respiratory Care Jan. 2000, vol. 45, No. 1: 95-100.
Meyers et al., "Chronic obstructive pulmonary disease 10: Bullectomy, lung volume reduction surgery, and transplantation for patients with chronic obstructive pulmonary disease", Thorax 2003; 58: 634-638.

U.S. Department of Health and Human Services; National Institutes of Health National Heart, Lung, and Blood Institute; "Chronic Obstructive Pulmonary Disease", NIH Publication No. 03-5229 Mar. 2003: 1-6.

Petty, Thomas L., "The history of COPD", International Journal of COPD 2006; 1(1): 3-14.

Polkey, M. J., "Surgical procedures in emphysema: any impact on dynamic hyperinflation?" European Respiratory Review 2006; 15(100): 96-98.

Polkey, M. J., "Bronchoscopic lung volume reduction", European Respiratory Review 2006; 15(100): 99-103.

Rendina et al., "Feasibility and safety of the airway bypass procedure for patients with emphysema", The Journal of Thoracic and Cardiovascular Surgery 2003; 125: 1294-1299.

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&Ing=e...> May 2, 2007.

Shah et al., "Surgical Treatment of Bulbous Emphysema: Experience with the Brompton Technique", Annals of Thoracic Surgery 1994; 58: 1452-1456.

Snell et al., "The Potential for Bronchoscopic Lung Volume Reduction Using Bronchial Prosteses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988. 94(6): 1289-1290.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.

Woolcock et al., "Mechanical factors influencing collateral ventilation in human, dog, and pig lungs", Journal of Applied Physiology 1971, 30: 99-115.

Woodring et al., "Pneumothorax ex vacuo", Chest 1996, 110: 1102-1105.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

Eloesser, "An Operation for Tuberculous Empyema", Chest 1935; 1: 8-23.

Hogg et al., "The Resistance of Collateral Channels in Excised Human Lungs", Journal of Clinical Investigation 1969; 48: 421-431.

Mineo et al., "Awake Nonresectional Lung Volume Reduction Surgery", Annals of Surgery 2006; 243: 131-136.

Monaldi, V., "Endocavitary Aspiration: Its Practical Application", Tubercle 1947: 223-228.

Monaldi, V., "Endocavitary Aspiration in the Treatment of Lung Abscess", Chest 1956; 29: 193-201.

Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.

Parker et al., "Percutaneous small bore catheter drainage in the management of lung abscesses", Chest 1987; 92: 213-218.

Shim et al., "Percutaneous Drainage of Lung Abscess", Lung 1990; 168: 201-207.

Stewart et al., "Decompression of Giant Bulla in Acute Pneumonia: Surgical Palliation Prior to Definitive Management", Ann Thoracic Surg 2006; 82: 2308-2309.

Symbas et al., "Nontuberculous Pleural Empyema in Adults, The Role of a Modified Eloesser Procedure in Its Management", The Annals of Thoracic Surgery 1971; 12: 69-78.

Thourani et al., "Twenty-six Years of Experience With the Modified Eloesser Flap", Ann Thorac Surg 2003; 76: 401-406.

Vainrub et al., "Percutaneous Drainage of Lung Abscess", American Review of Respiratory Disease 1978; 117: 153-160.

Yellin et al., "Percutaneous Tube Drainage: The Treatment of Choice for Refractory Lung Abscess", The Annals of Thoracic Surgery 1985; 39: 266-270.

* cited by examiner

METHOD FOR TREATING CHRONIC OBSTRUCTIVE PULMONARY DISEASE

CROSS REFERENCE TO RELATED APPLICATIONS

This application claims the benefit of Provisional Application No. 60/468,415 filed May 7, 2003.

BACKGROUND OF THE INVENTION

1. Field of the Invention

The present invention relates to systems and methods for removing trapped air in emphysematous lungs, and more particularly, to systems and methods for removing trapped air in emphysematous hyperinflated lungs by bypassing non-patent airways via a conduit through the outer pleural layer of the lung to a containment/trap device. The present invention also relates to systems and methods for chemical pleurodesis.

2. Discussion of the Related Art

As a result of studies that date back to the 1930's and particularly studies conducted in the 1960's and early 1970's, it has been determined that long-term continuous oxygen therapy is beneficial in the treatment of hypoxemic patients with chronic obstructive pulmonary disease. In other words, a patient's life and quality of life can be improved by providing a constant supplemental supply of oxygen to the patient's lungs.

However, with the desire to contain medical costs, there is a growing concern that the additional cost of providing continuous oxygen therapy for chronic lung disease will create an excessive increase in the annual cost of oxygen therapy. Thus, it is desirable that oxygen therapy, when provided, be as cost effective as possible.

The standard treatment for patients requiring supplemental oxygen is still to deliver oxygen from an oxygen source by means of a nasal cannula. Such treatment, however, requires a large amount of oxygen, which is wasteful and can cause soreness and irritation to the nose, as well as being potentially aggravating. Other undesirable effects have also been reported. Various other medical approaches which have been proposed to help reduce the cost of continuous oxygen therapy have been studied.

Various devices and methods have been devised for performing emergency cricothyroidotomies and for providing a tracheotomy tube so that a patient whose airway is otherwise blocked may continue to breath. Such devices are generally intended only for use with a patient who is not breathing spontaneously and are not suitable for the long term treatment of chronic lung disease. Typically, such devices are installed by puncturing the skin to create a hole into the cricoid membrane of the larynx above the trachea into which a relatively large curved tracheotomy tube is inserted. As previously described, the use of such tubes has been restricted medically to emergency situations where the patient would otherwise suffocate due to the blockage of the airway. Such emergency tracheotomy tubes are not suitable for long term therapy after the airway blockage is removed.

Other devices which have been found satisfactory for emergency or ventilator use are described in U.S. Pat. No. 953,922 to Rogers; U.S. Pat. No. 2,873,742 to Shelden; U.S. Pat. No. 3,384,087 to Brummelkamp; U.S. Pat. No. 3,511,243 to Toy; U.S. Pat. No. 3,556,103 to Calhoun; U.S. Pat. No. 2,991,787 to Shelden, et al; U.S. Pat. No. 3,688,773 to Weiss; 3,817,250 to Weiss, et al.; and U.S. Pat. No. 3,916,903 to Pozzi.

Although tracheotomy tubes are satisfactory for their intended purpose, they are not intended for chronic usage by outpatients as a means for delivering supplemental oxygen to spontaneously breathing patients with chronic obstructive pulmonary disease. Such tracheotomy tubes are generally designed so as to provide the total air supply to the patient for a relatively short period of time. The tracheotomy tubes are generally of rigid or semi-rigid construction and of caliber ranging from 2.5 mm outside diameter in infants to 15 mm outside diameter in adults. They are normally inserted in an operating room as a surgical procedure or during emergency situations, through the crico-thyroid membrane where the tissue is less vascular and the possibility of bleeding is reduced. These devices are intended to permit passage of air in both directions until normal breathing has been restored by other means.

Another type of tracheotomy tube is disclosed in Jacobs, U.S. Pat. Nos. 3,682,166 and 3,788,326. The catheter described therein is placed over 14 or 16 gauge needle and inserted through the crico-thyroid membrane for supplying air or oxygen and vacuum on an emergency basis to restore the breathing of a non-breathing patient. The air or oxygen is supplied at 30 to 100 psi for inflation and deflation of the patient's lungs. The Jacobs catheter, like the other tracheotomy tubes previously used, is not suitable for long term outpatient use, and could not easily be adapted to such use.

Due to the limited functionality of tracheotomy tubes, transtracheal catheters have been proposed and used for long term supplemental oxygen therapy. For example the small diameter transtracheal catheter (16 gauge) developed by Dr. Henry J. Heimlich (described in THE ANNALS OF OTOLOGY, RHINOLOGY & LARYNGOLOGY, November-December 1982; Respiratory Rehabilitation with Transtracheal Oxygen System) has been used by the insertion of a relatively large cutting needle (14 gauge) into the trachea at the mid-point between the cricothyroid membrane and the sternal notch. This catheter size can supply oxygen up to about 3 liters per minute at low pressures, such as 2 psi which may be insufficient for patients who require higher flow rates. It does not, however, lend itself to outpatient use and maintenance, such as periodic removal and cleaning, primarily because the connector between the catheter and the oxygen supply hose is adjacent and against the anterior portion of the trachea and cannot be easily seen and manipulated by the patient. Furthermore, the catheter is not provided with positive means to protect against kinking or collapsing which would prevent its effective use on an outpatient basis. Such a feature is not only desirable but necessary for long term outpatient and home care use. Also, because of its structure, i.e. only one exit opening, the oxygen from the catheter is directed straight down the trachea toward the bifurcation between the bronchi. Because of the normal anatomy of the bronchi wherein the left bronchus is at a more acute angle to the trachea than the right bronchus, more of the oxygen from that catheter tends to be directed into the right bronchus rather than being directed or mixed for more equal utilization by both bronchi. Also, as structured, the oxygen can strike the carina, resulting in an undesirable tickling sensation and cough. In addition, in such devices, if a substantial portion of the oxygen is directed against the back wall of the trachea causing erosion of the mucosa in this area which may cause chapping and bleeding. Overall, because of the limited output from the device, it may not operate to supply sufficient supplemental oxygen when the patient is exercising or otherwise quite active or has severe disease.

Diseases associated with chronic obstructive pulmonary disease include chronic bronchitis and emphysema. One aspect of an emphysematous lung is that the communicating flow of air between neighboring air sacs is much more prevalent as compared to healthy lungs. This phenomenon is known as collateral ventilation. Another aspect of an emphysematous lung is that air cannot be expelled from the native airways due to the loss of tissue elastic recoil and radial support of the airways. Essentially, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state where an individual can only take short shallow breaths. Essentially, air is not effectively expelled and stale air accumulates in the lungs. Once the stale air accumulates in the lungs, the individual is deprived of oxygen.

Currently, treatments for chronic obstructive pulmonary disease include bronchodilating drugs, oxygen therapy as described above, and lung volume reduction surgery. Bronchodilating drugs only work on a percentage of patients with chronic obstructive pulmonary disease and generally only provides short term relief. Oxygen therapy is impractical for the reasons described above, and lung volume reduction surgery is an extremely traumatic procedure that involves removing part of the lung. The long term benefits of lung volume reduction surgery are not fully known.

Accordingly, there exists a need for increasing the expiratory flow from an individual suffering from chronic obstructive pulmonary disease.

SUMMARY OF THE INVENTION

The present invention overcomes the disadvantages associated with treating chronic obstructive pulmonary disease, as briefly described above, by utilizing the phenomenon of collateral ventilation to increase the expiratory flow from a diseased lung.

In accordance with one aspect, the present invention is directed to a device for the local delivery of a pleurodesis agent, the device comprising a catheter having one or more fluid carrying conduits and a distal tip attached to and in fluid communication with the catheter, the distal tip being sized and configured to deliver a pleurodesis agent to a predetermined area in a pleural space of a patient.

In accordance with another aspect, the present invention is directed to a device for the local delivery of a pleurodesis agent, the device comprising an implantable medical device for implantation at a predetermined site in a pleural space of a patient and a pleurodesis agent affixed to the implantable medical device.

The long term oxygen therapy system of the present invention delivers oxygen directly to diseased sites in a patient's lungs. Long term oxygen therapy is widely accepted as the standard treatment for hypoxia caused by chronic obstructive pulmonary disease, for example, pulmonary emphysema. Pulmonary emphysema is a chronic obstructive pulmonary disease wherein the alveoli of the lungs lose their elasticity and the walls between adjacent alveoli are destroyed. As more and more alveoli walls are lost, the air exchange surface area of the lungs is reduced until air exchange becomes seriously impaired. The combination of mucus hypersecretion and dynamic air compression is a mechanism of airflow limitation in chronic obstructive pulmonary disease. Dynamic air compression results from the loss of tethering forces exerted on the airway due to the reduction in lung tissue elasticity. Essentially, stale air accumulates in the lungs, thereby depriving the individual of oxygen. Various methods may be utilized to determine the location or locations of the diseased tissue, for example, computerized axial tomography or CAT scans, magnetic resonance imaging or MRI, positron emission tomograph or PET, and/or standard X-ray imaging. Once the location or locations of the diseased tissue are located, anastomotic openings are made in the thoracic cavity and lung or lungs and one or more oxygen carrying conduits are positioned and sealed therein. The one or more oxygen carrying conduits are connected to an oxygen source which supplies oxygen under elevated pressure directly to the diseased portion or portions of the lung or lungs. The pressurized oxygen essentially displaces the accumulated air and is thus more easily absorbed by the alveoli tissue. In addition, the long term oxygen therapy system may be configured in such a way as to provide collateral ventilation bypass in addition to direct oxygen therapy. In this configuration, an additional conduit may be connected between the main conduit and the individual's trachea with the appropriate valve arrangement. In this configuration, stale air may be removed through the trachea when the individual exhales since the trachea is directly linked with the diseased site or sites in the lung via the conduits.

The long term oxygen therapy system of the present invention improves oxygen transfer efficiency in the lungs thereby reducing oxygen supply requirements, which in turn reduces the patient's medical costs. The system also allows for improved self-image, improved mobility, greater exercise capability and is easily maintained.

The above-described long term oxygen therapy system may be utilized to effectively treat hypoxia caused by chronic obstructive pulmonary disease; however, other means may be desirable to treat other aspects of the disease. As set forth above, emphysema is distinguished as irreversible damage to lung tissue. The breakdown of lung tissue leads to the reduced ability for the lungs to recoil. The tissue breakdown also leads to the loss of radial support of the airways. Consequently, the loss of elastic recoil of the lung tissue contributes to the inability for individuals with emphysema to exhale completely. The loss of radial support of the airways also allows a collapsing phenomenon to occur during the expiratory phase of breathing. This collapsing phenomenon also intensifies the inability for individuals to exhale completely. As the inability to exhale increases, residual volume in the lungs also increases. This then causes the lung to establish in a hyperinflated state wherein an individual can only take short shallow breaths.

The collateral ventilation bypass trap system of the present invention utilizes the above-described collateral ventilation phenomenon to increase the expiratory flow from a diseased lung or lungs, thereby treating another aspect of chronic obstructive pulmonary disease. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allow the entrapped air to bypass the native airways and be expelled to a containment system outside of the body.

In order for the system to be effective, the components of the system are preferably sealed to the lung. Accordingly, the localized pleurodesis chemical delivery system of the present invention is utilized to create a pleurodesis in the area or areas of the lung that are most collaterally ventilated. Various chemicals, agents and/or compounds may be delivered via catheter based delivery systems or via implantable medical devices.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
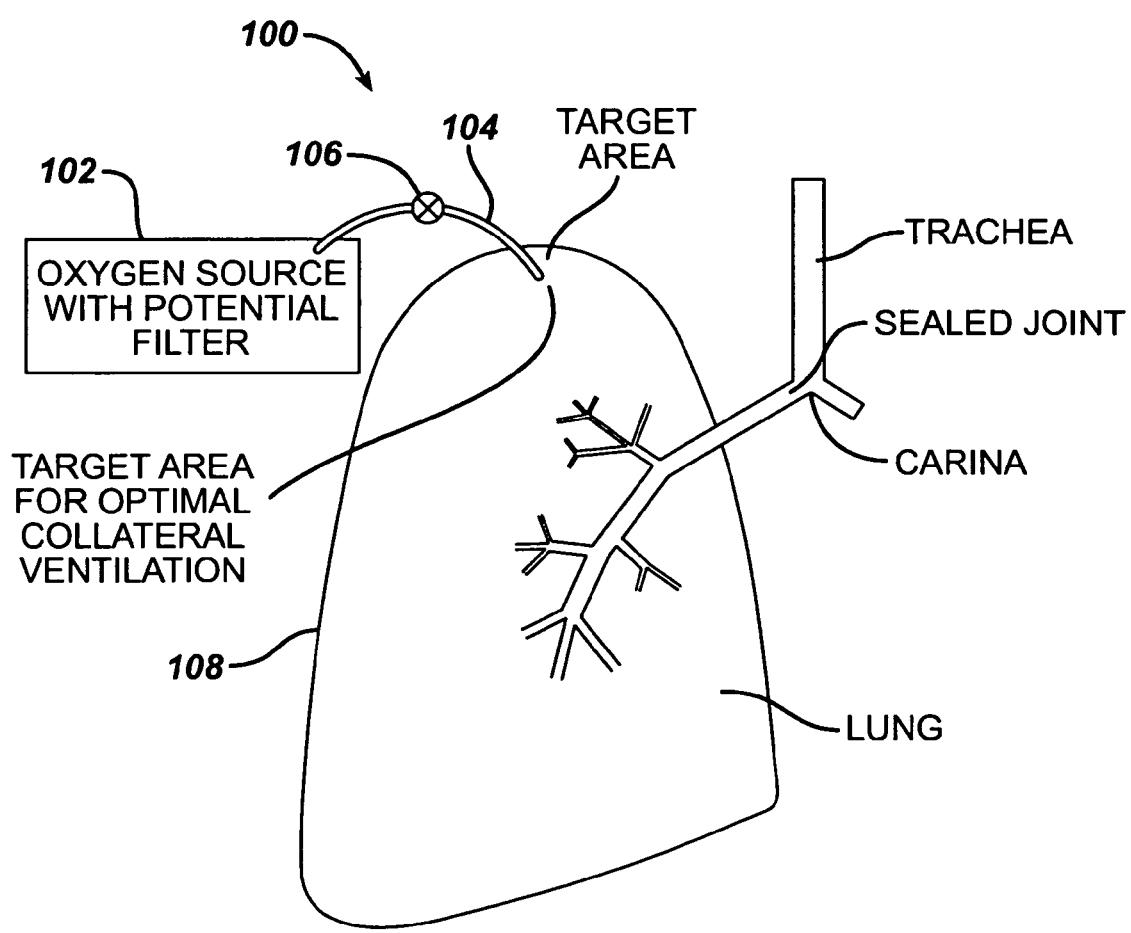
FIG. 1 is a diagrammatic representation of a first exemplary embodiment of the long term oxygen therapy system in accordance with the present invention.

Air typically enters the mammalian body through the nostrils and flows into the nasal cavities. As the air passes through the nostrils and nasal cavities, it is filtered, moistened and raised or lowered to approximately body temperature. The back of the nasal cavities is continuous with the pharynx (throat region); therefore, air may reach the pharynx from the nasal cavities or from the mouth. Accordingly, if equipped, the mammal may breath through its nose or mouth. Generally air from the mouth is not as filtered or temperature regulated as air from the nostrils. The air in the pharynx flows from an opening in the floor of the pharynx and into the larynx (voice box). The epiglottis automatically closes off the larynx during swallowing so that solids and/or liquids enter the esophagus rather than the lower air passageways or airways. From the larynx, the air passes into the trachea, which divides into two branches, referred to as the bronchi. The bronchi are connected to the lungs.

The lungs are large, paired, spongy, elastic organs, which are positioned in the thoracic cavity. The lungs are in contact with the walls of the thoracic cavity. In humans, the right lung comprises three lobes and the left lung comprises two lobes. Lungs are paired in all mammals, but the number of lobes or sections of lungs varies from mammal to mammal. Healthy lungs, as discussed below, have a tremendous surface area for gas/air exchange. Both the left and right lung is covered with a pleural membrane. Essentially, the pleural membrane around each lung forms a continuous sac that encloses the lung. A pleural membrane also forms a lining for the thoracic cavity. The space between the pleural membrane forming the lining of the thoracic cavity and the pleural membranes enclosing the lungs is referred to as the pleural cavity. The pleural cavity comprises a film of fluid that serves as a lubricant between the lungs and the chest wall.

In the lungs, the bronchi branch into a multiplicity of smaller vessels referred to as bronchioles. Typically, there are more than one million bronchioles in each lung. Each bronchiole ends in a cluster of extremely small air sacs referred to as alveoli. An extremely thin, single layer of epithelial cells lining each alveolus wall and an extremely thin, single layer of epithelial cells lining the capillary walls separate the air/gas in the alveolus from the blood. Oxygen molecules in higher concentration pass by simple diffusion through the two thin layers from the alveoli into the blood in the pulmonary capillaries. Simultaneously, carbon dioxide molecules in higher concentration pass by simple diffusion through the two thin layers from the blood in the pulmonary capillaries into the alveoli.

Breathing is a mechanical process involving inspiration and expiration. The thoracic cavity is normally a closed system and air cannot enter or leave the lungs except through the trachea. If the chest wall is somehow compromised and air/gas enters the pleural cavity, the lungs will typically collapse. When the volume of the thoracic cavity is increased by the contraction of the diaphragm, the volume of the lungs is also increased. As the volume of the lungs increase, the pressure of the air in the lungs falls slightly below the pressure of the air external to the body (ambient air pressure). Accordingly, as a result of this slight pressure differential, external or ambient air flows through the respiratory passageways described above and fills the lungs until the pressure equalizes. This process is inspiration. When the diaphragm is relaxed, the volume of the thoracic cavity decreases, which in turn decreases the volume of the lungs. As the volume of the lungs decrease, the pressure of the air in the lungs rises slightly above the pressure of the air external to the body. Accordingly, as a result of this slight pressure differential, the air in the alveoli is expelled through the respiratory passageways until the pressure equalizes. This process is expiration.

Continued insult to the respiratory system may result in various diseases, for example, chronic obstructive pulmonary disease. Chronic obstructive pulmonary disease is a persistent obstruction of the airways caused by chronic bronchitis and pulmonary emphysema. In the United States alone, approximately fourteen million people suffer from some form of chronic obstructive pulmonary disease and it is in the top ten leading causes of death.

Chronic bronchitis and acute bronchitis share certain similar characteristics; however, they are distinct diseases. Both chronic and acute bronchitis involve inflammation and constriction of the bronchial tubes and the bronchioles; however, acute bronchitis is generally associated with a viral and/or bacterial infection and its duration is typically much shorter than chronic bronchitis. In chronic bronchitis, the bronchial tubes secrete too much mucus as part of the body's defensive mechanisms to inhaled foreign substances. Mucus membranes comprising ciliated cells (hair like structures) line the trachea and bronchi. The ciliated cells or cilia continuously push or sweep the mucus secreted from the mucus membranes in a direction away from the lungs and into the pharynx, where it is periodically swallowed. This sweeping action of the cilia functions to keep foreign matter from reaching the lungs. Foreign matter that is not filtered by the nose and larynx, as described above, becomes trapped in the mucus and is propelled by the cilia into the pharynx. When too much mucus is secreted, the ciliated cells may become damaged, leading to a decrease in the efficiency of the cilia to sweep the bronchial tubes and trachea of the mucus containing the foreign matter. This in turn causes the bronchioles to become constricted and inflamed and the individual becomes short of breath. In addition, the individual will develop a chronic cough as a means of attempting to clear the airways of excess mucus.

Individuals who suffer from chronic bronchitis may develop pulmonary emphysema. Pulmonary emphysema is a disease in which the alveoli walls, which are normally fairly rigid structures, are destroyed. The destruction of the alveoli walls is irreversible. Pulmonary emphysema may be caused by a number of factors, including chronic bronchitis, long term exposure to inhaled irritants, e.g. air pollution, which damage the cilia, enzyme deficiencies and other pathological conditions. In pulmonary emphysema, the alveoli of the lungs lose their elasticity, and eventually the walls between adjacent alveoli are destroyed. Accordingly, as more and more alveoli walls are lost, the air exchange (oxygen and carbon dioxide) surface area of the lungs is reduced until air exchange becomes seriously impaired. The combination of mucus hypersecretion and dynamic airway compression are mechanisms of airflow limitation in chronic obstructive pulmonary disease. Dynamic airway compression results from the loss of tethering forces exerted on the airway due to the reduction in lung tissue elasticity. Mucus hypersecretion is described above with respect to bronchitis. In other words, the breakdown of lung tissue leads to the reduced ability of the lungs to recoil and the loss of radial support of the airways. Consequently, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state where an individual can only take short shallow breaths. Essentially, air is not effectively expelled and stale air accumulates in the lungs. Once the stale air accumulates in the lungs, the individual is deprived of oxygen. There is no cure for pulmonary emphysema, only various treatments, including exercise, drug therapy, such as bronchodilating agents, lung volume reduction surgery and long term oxygen therapy.

As described above, long term oxygen therapy is widely accepted as the standard treatment for hypoxia caused by chronic obstructive pulmonary disease. Typically, oxygen therapy is prescribed using a nasal cannula. There are disadvantages associated with using the nasal cannula. One disadvantage associated with utilizing nasal cannula is the significant loss of oxygen between the cannula and the nose, which in turn equates to more frequent changes in the oxygen source, or higher energy requirements to generate more oxygen. Another disadvantage associated with utilizing nasal cannula is the fact that the cannulas may cause the nasal passages to become dry, cracked and sore.

Transtracheal oxygen therapy has become a viable alternative to long term oxygen therapy. Transtracheal oxygen therapy delivers oxygen directly to the lungs using a catheter that is placed through and down the trachea. Due to the direct nature of the oxygen delivery, a number of advantages are achieved. These advantages include lower oxygen requirements due to greater efficiency, increased mobility, greater exercise capability and improved self image.

The long term oxygen therapy system and method of the present invention may be utilized to deliver oxygen directly into the lung tissue in order to optimize oxygen transfer efficiency in the lungs. In other words, improved efficiency may be achieved if oxygen were to be delivered directly into the alveolar tissue in the lungs. In emphysema, alveoli walls are destroyed, thereby causing a decrease in air exchange surface area. As more alveoli walls are destroyed, collateral ventilation resistance is lowered. In other words, pulmonary emphysema causes an increase in collateral ventilation and to a certain extent, chronic bronchitis also causes an increase in collateral ventilation. Essentially, in an emphysematous lung, the communicating flow of air between neighboring air sacs (alveoli), known as collateral ventilation, is much more prevalent as compared to a normal lung. Since air cannot be expelled from the native airways due to the loss of tissue elastic recoil and radial support of the airways (dynamic collapse during exhalation), the increase in collateral ventilation does not significantly assist an individual in breathing. The individual develops dsypnea. Accordingly, if it can be determined where collateral ventilation is occurring, then the diseased lung tissue may be isolated and the oxygen delivered to this precise location or locations. Various methods may be utilized to determine the diseased tissue locations, for example, computerized axial tomography or CAT scans, magnetic resonance imaging or MRI, positron emission tomograph or PET, and/or standard X-ray imaging. Once the diseased tissue is located, pressurized oxygen may be directly delivered to these diseased areas and more effectively and efficiently forced into the lung tissue for air exchange.

FIG. 1 illustrates a first exemplary long term oxygen therapy system 100. The system 100 comprises an oxygen source 102, an oxygen carrying conduit 104 and a one-way valve 106. The oxygen source 102 may comprise any suitable device for supplying filtered oxygen under adjustably regulated pressures and flow rates, including pressurized oxygen tanks, liquid oxygen reservoirs, oxygen concentrators and the associated devices for controlling pressure and flow rate e.g. regulators. The oxygen carrying conduit 104 may comprise any suitable biocompatible tubing having a high resistance to damage caused by continuous oxygen exposure. The oxygen carrying conduit 104 comprises tubing having an inside diameter in the range from about 1/16 inch to about 1/2 inch and more preferably from about 1/8 inch to about 1/4 inch. The one-way valve 106 may comprise any suitable, in-line mechanical valve which allows oxygen to flow into the lungs 108 through the oxygen carrying conduit 104, but not from the lungs 108 back into the oxygen source 102. For example, a simple check valve may be utilized. As illustrated in FIG. 1, the oxygen carrying conduit 104 passes through the lung 108 at the site determined to have the highest degree of collateral ventilation.

The exemplary system 100 described above may be modified in a number of ways, including the use of an in-line filter. In this exemplary embodiment, both oxygen and air may flow through the system. In other words, during inhalation, oxygen is delivered to the lungs through the oxygen carrying conduit 104 and during exhalation, air from the lungs flow through the oxygen carrying conduit 104. The in-line filter would trap mucus and other contaminants, thereby preventing a blockage in the oxygen source 102. In this exemplary embodiment, no valve 106 would be utilized. The flow of oxygen into the lungs and the flow of air from the lungs is based on pressure differentials.

In order for the exemplary long term oxygen therapy system 100 to function, an air-tight seal is preferably maintained where the oxygen carrying conduit 104 passes through the thoracic cavity and lung. This seal is maintained in order to sustain the inflation/functionality of the lungs. If the seal is breached, air can enter the cavity and cause the lungs to collapse as described above.

A method to create this seal comprises forming adhesions between the visceral pleura of the lung and the inner wall of the thoracic cavity. This may be achieved using either chemical methods, including irritants such as Doxycycline and/or Bleomycin, surgical methods, including pleurectomy or horoscope talc pleurodesis, or radiotherapy methods, including radioactive gold or external radiation. All of these methods are known in the relevant art for creating pleurodesis. With a seal created at the site for the ventilation bypass, an intervention may be safely performed without the danger of creating a pneumothorax of the lung.

Figure 2:
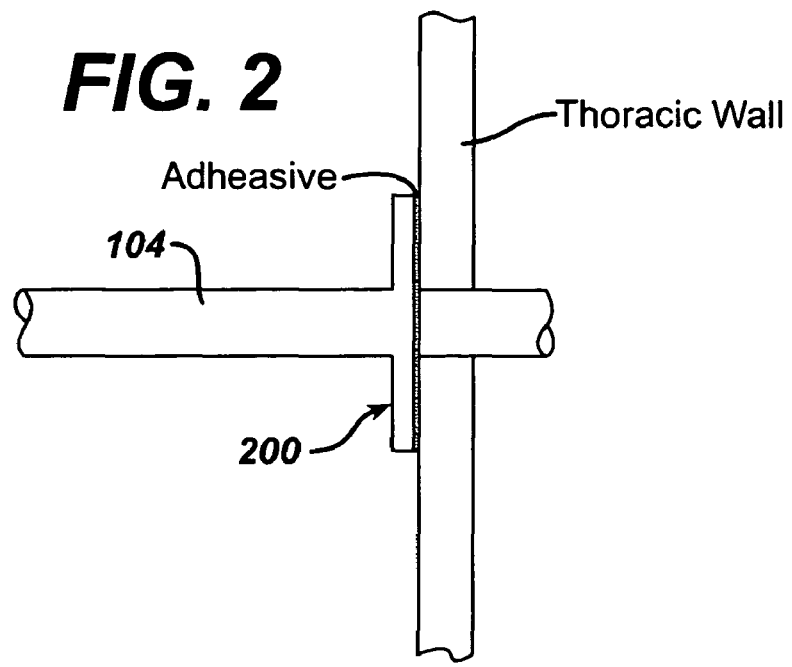
FIG. 2 is a diagrammatic representation of a first exemplary embodiment of a sealing device utilized in conjunction with the long term oxygen therapy system of the present invention.

Similarly to ostomy pouches or bags, the oxygen carrying conduit 104 may be sealed to the skin at the site of the ventilation bypass. In one exemplary embodiment, illustrated in FIG. 2, the oxygen carrying conduit 104 may be sealed to the skin of the thoracic wall utilizing an adhesive. As illustrated, the oxygen carrying conduit 104 comprises a flange 200 having a biocompatible adhesive coating on the skin contacting surface. The biocompatible adhesive would provide a fluid tight seal between the flange 200 and the skin or epidermis of the thoracic wall. In a preferred embodiment, the biocompatible adhesive provides a temporary fluid tight seal such that the oxygen carrying conduit 104 may be disconnected from the ventilation bypass site. This would allow for the site to be cleaned and for the long term oxygen therapy system 100 to undergo periodic maintenance.

Figure 3:
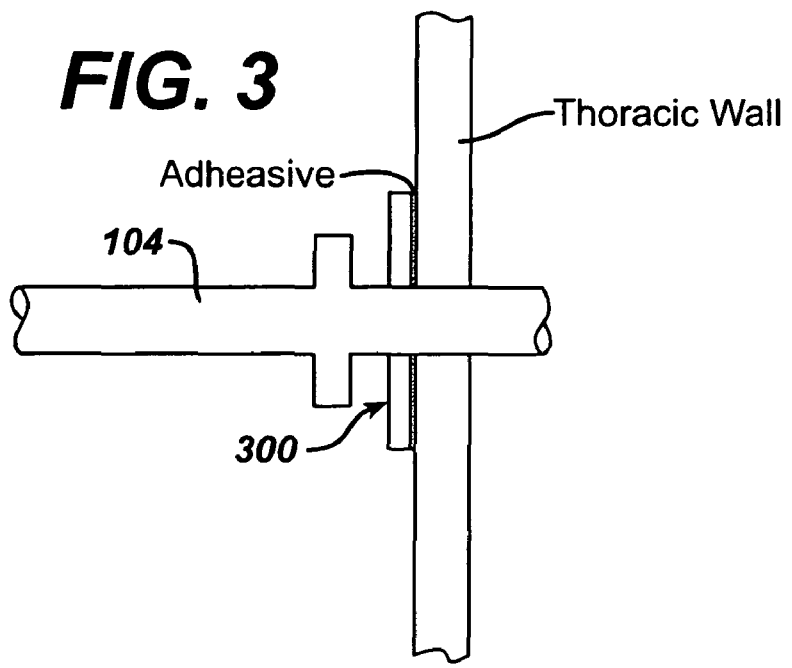
FIG. 3 is a diagrammatic representation of a second exemplary embodiment of a sealing device utilized in conjunction with the long term oxygen therapy system of the present invention.

FIG. 3 illustrates another exemplary embodiment for sealing the oxygen carrying conduit 104 to the skin of the thoracic wall at the site of the ventilation bypass. In this exemplary embodiment, a coupling plate 300 is sealed to the skin at the site of the ventilation bypass by a biocompatible adhesive coating or any other suitable means. The oxygen carrying conduit 104 is then connected to the coupling plate 300 by any suitable means, including threaded couplings and locking rings. The exemplary embodiment also allows for cleaning of the site and maintenance of the system 100.

Figure 4:
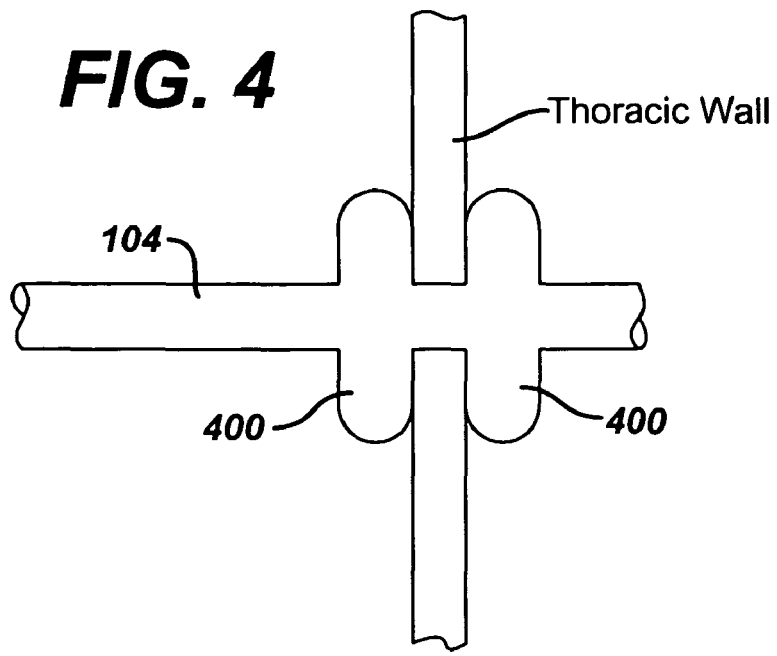
FIG. 4 is a diagrammatic representation of a third exemplary embodiment of a sealing device utilized in conjunction with the long term oxygen therapy system of the present invention.

FIG. 4 illustrates yet another exemplary embodiment for sealing the oxygen carrying conduit 104 to the skin of the thoracic wall at the site of the ventilation bypass. In this exemplary embodiment, balloon flanges 400 may be utilized to create the seal. The balloon flanges 400 may be attached to the oxygen carrying conduit 104 such that in the deflated state, the oxygen carrying conduit 104 and one of the balloon flanges passes through the ventilation bypass anastomosis. The balloon flanges 400 are spaced apart a sufficient distance such that the balloon flanges remain on opposite sides of the thoracic wall. When inflated, the balloons expand and form a fluid tight seal by sandwiching the thoracic wall. Once again, this exemplary embodiment allows for easy removal of the oxygen carrying conduit 104.

Figure 5:
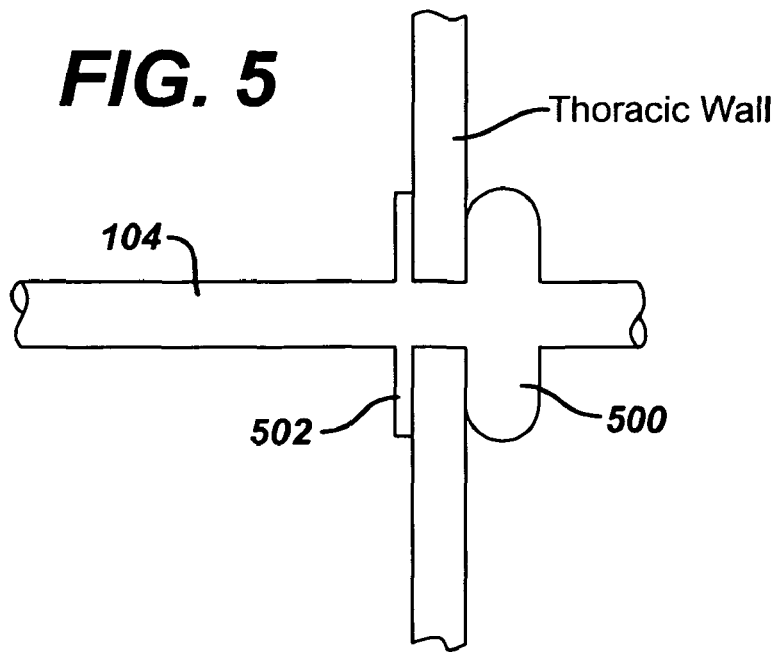
FIG. 5 is a diagrammatic representation of a fourth exemplary embodiment of a sealing device utilized in conjunction with the long term oxygen therapy system of the present invention.

FIG. 5 illustrates yet another exemplary embodiment for sealing the oxygen carrying conduit 104 to the skin of the thoracic wall at the site of the ventilation bypass. In this exemplary embodiment, a single balloon flange 500 is utilized in combination with a fixed flange 502. The balloon flange 500 is connected to the oxygen carrying conduit 104 in the same manner as described above. In this exemplary embodiment, the balloon flange 500, when inflated, forms the fluid tight seal. The fixed flange 502, which is maintained against the skin of the thoracic wall, provides the structural support against which the balloon exerts pressure to form the seal.

Figure 6:
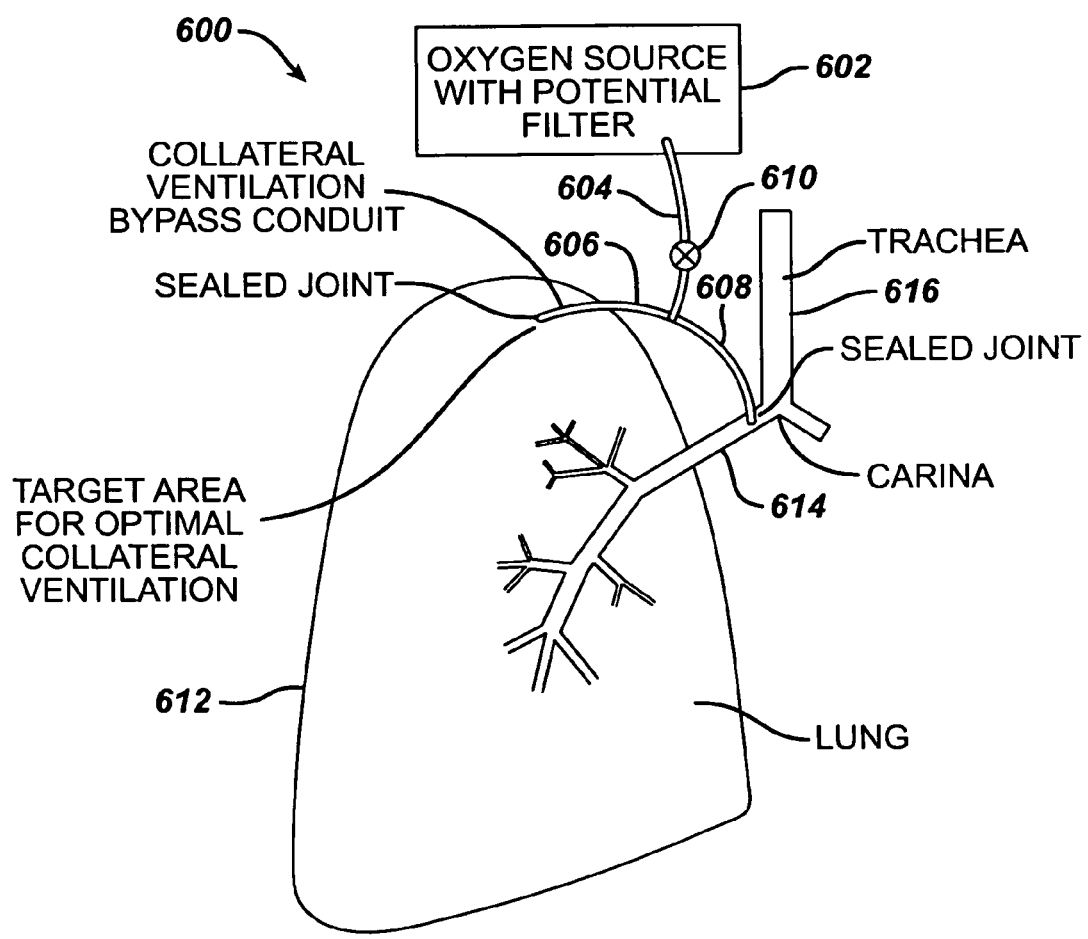
FIG. 6 is a diagrammatic representation of a second exemplary embodiment of the long term oxygen therapy system in accordance with the present invention.

If an individual has difficulty exhaling and requires additional oxygen, collateral ventilation bypass may be combined with direct oxygen therapy. FIG. 6 illustrates an exemplary embodiment of a collateral ventilation bypass/direct oxygen therapy system 600. The system 600 comprises an oxygen source 602, an oxygen carrying conduit 604 having two branches 606 and 608, and a control valve 610. The oxygen source 602 and oxygen carrying conduit 604 may comprise components similar to the above-described exemplary embodiment illustrated in FIG. 1. In this exemplary embodiment, when the individual inhales, the valve 610 is open and oxygen flows into the lung 612 and into the bronchial tube 614. In an alternate exemplary embodiment, the branch 608 may be connected to the trachea 616. Accordingly, during inhalation oxygen flows to the diseased site in the lung or lungs and to other parts of the lung through the normal bronchial passages. During exhalation, the valve 610 is closed so that no oxygen is delivered and air in the diseased portion of the lung may flow from the lung 612, through one branch 606 and into the second branch 608 and finally into the bronchial tube 616. In this manner, stale air is removed and oxygen is directly delivered. Once again, as described above, the flow of oxygen and air is regulated by simple pressure differentials.

The connection and sealing of the oxygen carrying conduit 604 and branches 606, 608 to the lung 612 and bronchial tube 614 may be made in a manner similar to that described above.

The above-described long term oxygen therapy system may be utilized to effectively treat hypoxia caused by chronic obstructive pulmonary disease; however, other means may be desirable to treat other aspects of the disease. As set forth above, emphysema is distinguished as irreversible damage to lung tissue. The breakdown of lung tissue leads to the reduced ability for the lungs to recoil. The tissue breakdown also leads to the loss of radial support of the native airways. Consequently, the loss of elastic recoil of the lung tissue contributes to the inability for individuals with emphysema to exhale completely. The loss of radial support of the native airways also allows a collapsing phenomenon to occur during the expiratory phase of breathing. This collapsing phenomenon also intensifies the inability for individuals to exhale completely. As the inability to exhale increases, residual volume in the lungs also increases. This then causes the lung to establish in a hyperinflated state wherein an individual can only take short shallow breaths.

The collateral ventilation bypass trap system of the present invention utilizes the above-described collateral ventilation phenomenon to increase the expiratory flow from a diseased lung or lungs, thereby treating another aspect of chronic obstructive pulmonary disease. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allows the entrapped air to bypass the native airways and be expelled to a containment system outside of the body.

Figure 7:
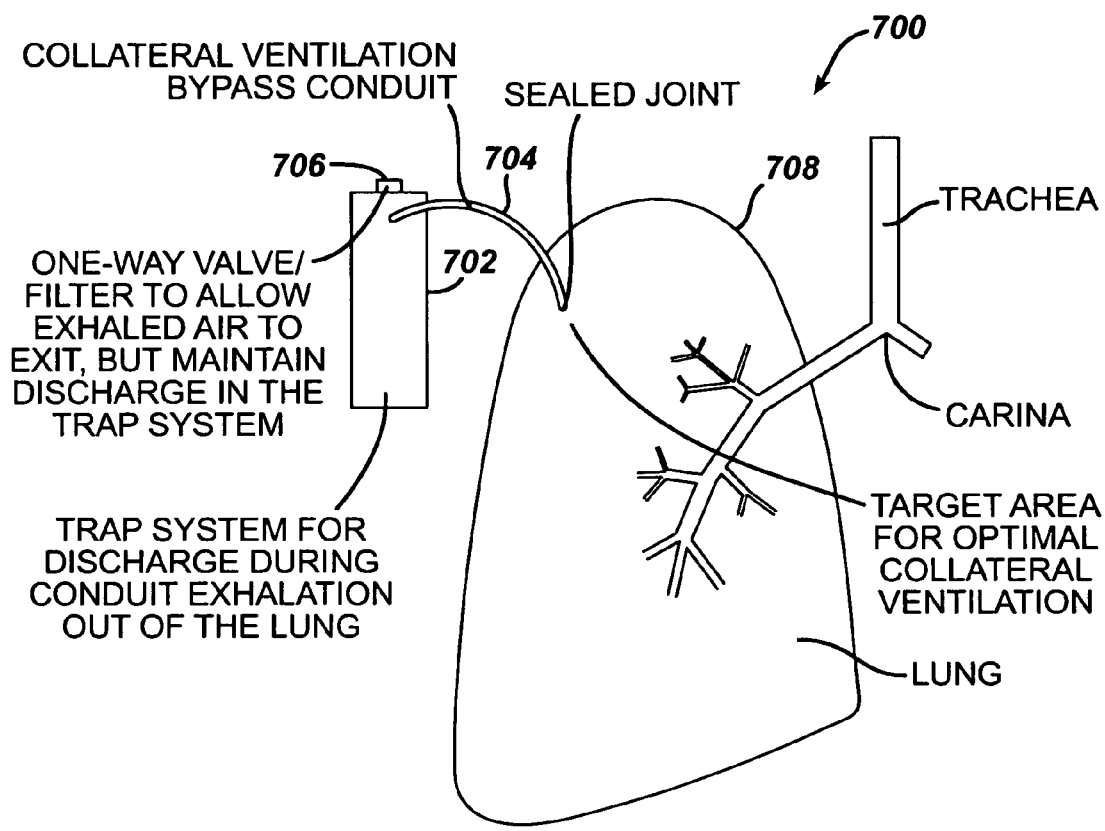
FIG. 7 is a diagrammatic representation of a first exemplary embodiment of a collateral ventilation bypass trap system in accordance with the present invention.

FIG. 7 illustrates a first exemplary collateral ventilation bypass trap system 700. The system 700 comprises a trap 702, an air carrying conduit 704 and a filter/one-way valve 706. The air carrying conduit 704 creates a fluid communication between an individual's lung 708 and the trap 702 through the filter/one-way valve 706. It is important to note that although a single conduit 704 is illustrated, multiple conduits may be utilized in each lung 708 if it is determined that there are more than one area of high collateral ventilation.

The trap 702 may comprise any suitable device for collecting discharge from the individual's lung or lungs 708. Essentially, the trap 702 is simply a containment vessel for temporarily storing discharge from the lungs, for example, mucous and other fluids that may accumulate in the lungs. The trap 702 may comprise any suitable shape and may be formed from any suitable metallic or non-metallic materials. Preferably, the trap 702 should be formed from a lightweight, non-corrosive material. In addition, the trap 702 should be designed in such a manner as to allow for effective and efficient cleaning. In one exemplary embodiment, the trap 702 may comprise disposable liners that may be removed when the trap 702 is full. The trap 702 may be formed from a transparent material or comprise an indicator window so that it may be easily determined when the trap 702 should be emptied or cleaned. A lightweight trap 702 increases the patient's mobility.

The filter/one-way valve 706 may be attached to the trap 702 by any suitable means, including threaded fittings or compression type fittings commonly utilized in compressor connections. The filter/one-way valve 706 serves a number of functions. The filter/one-way valve 706 allows the air from the individual's lung or lungs 708 to exit the trap 702 while maintaining the fluid discharge and solid particulate matter in the trap 702. This filter/one-way valve 706 would essentially maintain the pressure in the trap 702 below that of the pressure inside the individual's lung or lungs 708 so that the flow of air from the lungs 708 to the trap 702 is maintained in this one direction. The filter portion of the filter/one-way valve 706 may be designed to capture particulate matter of a particular size which is suspended in the air, but allows the clean air to pass therethrough and be vented to the ambient environment. The filter portion may also be designed in such a manner as to reduce the moisture content of the exhaled air.

The air carrying conduit 704 connects the trap 702 to the lung or lungs 708 of the patient through the filter/one-way valve 706. The air carrying conduit 704 may comprise any suitable biocompatible tubing having a resistance to the gases contained in air. The air carrying conduit 704 comprises tubing having an inside diameter in the range from about 1/16 inch to about ½ inch, and more preferably from about ⅛ inch to about ¼ inch. The filter/one-way valve 706 may comprise any suitable valve which allows air to flow from the lung or lungs 708 through the air carrying conduit 704, but not from the trap 702 back to the lungs 708. For example, a simple check valve may be utilized. The air carrying conduit 704 may be connected to the filter/one-way valve 706 by any suitable means. Preferably, a quick release mechanism is utilized so that the trap may be easily removed for maintenance. As illustrated in FIG. 7, the air carrying conduit 704 passes through the lung 708 at the site determined to have the highest degree of collateral ventilation. If more than one site is determined, multiple air carrying conduits 704 may be utilized. The connection of multiple air carrying conduits 704 to the filter/one-way valve 706 may be accomplished by any suitable means, including an octopus device similar to that utilized in scuba diving regulators.

The air carrying conduit 704 is preferably able to withstand and resist collapsing once in place. Since air will travel through the conduit 704, if the conduit is crushed and unable to recover, the effectiveness of the system is diminished. Accordingly, a crush recoverable material may be incorporated into the air carrying conduit 704 in order to make it crush recoverable. Any number of suitable materials may be utilized. For example, Nitinol incorporated into the conduit 704 will give the conduit collapse resistance and collapse recovery properties.

Expandable features at the end of the conduit 704 may be used to aid in maintaining contact and sealing the conduit 704 to the lung pleura. Nitinol incorporated into the conduit 704 will provide the ability to deliver the conduit 704 in a compressed state and then deployed in an expanded state to secure it in place. Shoulders at the end of the conduit may also provide a mechanical stop for insertion and an area for an adhesive/sealant to join as described in detail subsequently.

In order for the exemplary collateral ventilation bypass trap system 700 to function, an air-tight seal is preferably maintained where the air carrying conduit 704 passes through the thoracic cavity and lungs 708. This seal is maintained in order to sustain the inflation/functionality of the lungs. If the seal is breached, air can enter the cavity and cause the lungs to collapse. One exemplary method for creating the seal comprises forming adhesions between the visceral pleura of the lung and the inner wall of the thoracic cavity. This may be achieved using either chemical methods, including irritants such as Doxycycline and/or Bleomycin, surgical methods, including pleurectomy or thorascopic talc pleurodesis, or radiotherapy methods, including radioactive gold or external radiation. All of these methods are known in the relevant art for creating pleurodesis. In another alternate exemplary embodiment, a sealed joint between the air carrying conduit 704 and the outer pleural layer includes using various glues to help with the adhesion/sealing of the air carrying conduit 704. Currently, Focal Inc. markets a sealant available under the tradename Focal/Seal-L which is indicated for use on a lung for sealing purposes. Focal/Seal-L is activated by light in order to cure the sealant. Another seal available under the tradename Thorex, which is manufactured by Surgical Sealants Inc., is currently conducting a clinical trial for lung sealing indications. Thorex is a two-part sealant that has a set curing time after the two parts are mixed.

The creation of the opening in the chest cavity may be accomplished in a number of ways. For example, the procedure may be accomplished using an open chest procedure, aternotomy or thoracotomy. Alternately, the procedure may be accomplished using a laproscopic technique, which is less invasive. Regardless of the procedure utilized, the seal should be established while the lung is at least partially inflated in order to maintain a solid adhesive surface. The opening may then be made after the joint has been adequately created between the conduit component and the lung pleural surface. The opening should be adequate in cross-sectional area in order to provide sufficient decompression of the hyperinflated lung. This opening, as stated above, may be created using a number of different techniques such as cutting, piercing, dilating, blunt dissection, radio frequency energy, ultrasonic energy, microwave energy, or cryoblative energy.

The air carrying conduit 704 may be sealed to the skin at the site by any of the means and methods described above with respect to the oxygen carrying conduit 704 and illustrated in FIGS. 2 through 5.

In operation, when an individual exhales, the pressure in the lungs is greater than the pressure in the trap 702. Accordingly, the air in the highly collaterilized areas of the lung will travel through the air carrying conduit 704 to the trap 702. This operation will allow the individual to more easily and completely exhale.

In the above-described exemplary apparatus and procedure for increasing expiratory flow from a diseased lung using the phenomenon of collateral ventilation, there will be an optimal location to penetrate the outer pleura of the lung to access the most collaterally ventilated area or areas of the lung. As described above, there are a variety of techniques to locate the most collaterally ventilated area or areas of the lungs. Since a device or component of the apparatus functions to allow the air entrapped in the lung to bypass the native airways and be expelled outside of the body, it is particularly advantageous to provide an air-tight seal of the parietal (thoracic wall) and visceral (lung) pleurae. If a proper air-tight seal is not created between the device, parietal and visceral pleurae, then a pneumothorax (collapsed lung) may occur. Essentially, in any circumstance where the lung is punctured and a device inserted, an air-tight seal should preferably be maintained.

One way to achieve an air-tight seal is through pleurodesis, i.e. an obliteration of the pleural space. There are a number of pleurodesis methods, including chemical, surgical and radiological. In chemical pleurodesis, an agent such as tetracycline, doxycycline, bleomycin or nitrogen mustard may be utilized. In surgical pleurodesis, a pleurectomy or a thorascopic talc procedure may be performed. In radiological procedures, radioactive gold or external radiation may be utilized. In the present invention, chemical pleurodesis is utilized.

Exemplary devices and methods for delivering a chemical(s) or agent(s) in a localized manner for ensuring a proper air-tight seal of the above-described apparatuseis described below. The chemical(s), agent(s) and/or compound(s) are used to create a pleurodesis between the parietal and visceral pleura so that a component of the apparatus may penetrate through the particular area and not result in a pneumothorax. There are a number of chemical(s), agent(s) and/or compound(s) that may be utilized to create a pleurodesis in the pleural space. The chemical(s), agent(s) and/or compound(s) include talc, tetracycline, doxycycline, bleomycin and minocycline.

Figure 8:
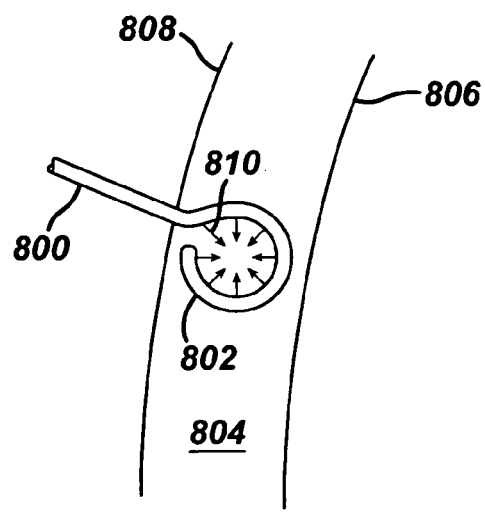
FIG. 8 is a diagrammatic representation of a first exemplary embodiment of a localized pleurodesis chemical delivery system.

In one exemplary embodiment, a modified drug delivery catheter may be utilized to deliver chemical(s), agent(s) and/or compound(s) to a localized area for creating a pleurodesis in that area. In this exemplary embodiment, the pleurodesis is formed and then the conduit 704, as illustrated in FIG. 7, is positioned in the lung 708 through the area of the pleurodesis. The drug delivery catheter provides a minimally invasive means for creating a localized pleurodesis. Referring to FIG. 8, there is illustrated an exemplary embodiment of a drug delivery catheter that may be utilized in accordance with the present invention. Any number of drug delivery catheters may be utilized. In addition, the distal tip of the catheter may comprise any suitable size, shape or configuration thereby enabling the formation of a pleurodesis having any size, shape or configuration.

As illustrated in FIG. 8, the catheter 800 is inserted into the patient such that the distal end 802 is positioned in the pleural space 804 between the thoracic wall 800 and the lung 808. In the illustrated exemplary embodiment, the distal end 802 of the catheter 800 comprises a substantially circular shape that would allow the chemical(s), agent(s) and/or compound(s) to be released towards the inner diameter of the substantially circular shape as indicated by arrows 810. The distal end 802 of the catheter 800 comprising a plurality of holes or openings 812 through which the chemical(s), agent(s) and/or compound(s) are released. As stated above, the distal end 802 may comprise any suitable size, shape or configuration. Once the chemical(s), agent(s) and/or compound(s) are delivered, the catheter 800 may be removed to allow for implantation of the conduit 704 (FIG. 7). Alternately, the catheter 800 may be utilized to facilitate delivery of the conduit 704.

The distal end or tip 802 of the catheter 800 should preferably maintain its desired size, shape and/or configuration once deployed in the pleural space. This may be accomplished in a number of ways. For example, the material forming the distal end 802 of the catheter 800 may be selected such that it has a certain degree of flexibility for insertion of the catheter 800 and a certain degree of shape memory such that it resumes its original or programmed shape once deployed. Any number of biocompatible polymers with these properties may be utilized. In an alternate embodiment, another material may be utilized. For example, a metallic material having shape memory characteristics may be integrated into the distal end 802 of the catheter 800. This metallic material may include nitinol or stainless steel. In addition, the metallic material may be radiopaque or comprise radiopaque markers. By having a radiopaque material or radiopaque markers, the catheter 800 may be viewed under x-ray fluoroscopy and aid in determining when the catheter 800 is at the location of the highest collateral ventilation.

In another alternate exemplary embodiment, a local drug delivery device may be utilized to deliver the pleurodesis chemical(s), agent(s) and/or compound(s). In this exemplary embodiment, the pleurodesis is formed and then the conduit 704, as illustrated in FIG. 7, is positioned in the lung 708 through the pleurodesis. In this exemplary embodiment, chemical(s), agent(s) and/or compound(s) may be affixed to an implantable medical device. The medical device is then implanted in the pleural cavity at a particular site and the chemical(s), agent(s) and/or compound(s) are released therefrom to form or create the pleurodesis.

Any of the above-described chemical(s), agent(s) and/or compound(s) may be affixed to the medical device. The chemical(s), agent(s) and/or compound(s) may be affixed to the medical device in any suitable manner. For example, the chemical(s), agent(s) and/or compound(s) may be coated on the device utilizing any number of well known techniques including, spin coating, spraying or dipping, they may be incorporated into a polymeric matrix that is affixed to the surface of the medical device, they may be impregnated into the outer surface of the medical device, they may be incorporated into holes or chambers in the medical device, they may be coated onto the surface of the medical device and then coated with a polymeric layer that acts as a diffusion barrier for controlled release of the chemical(s), agent(s) and/or compound(s), they may be incorporated directly into the material forming the medical device, or any combination of the above-described techniques. In another alternate embodiment, the medical device may be formed from a biodegradable material which elutes the chemical(s), agent(s) and/or compound(s) as the device degrades.

Figure 9:
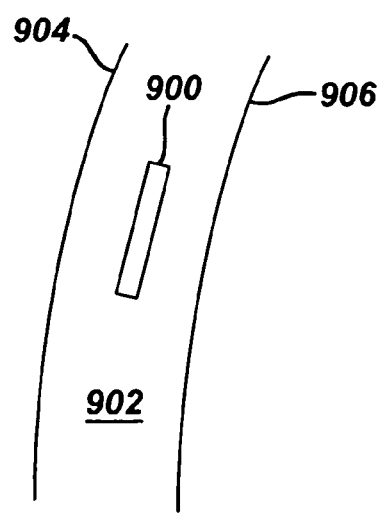
FIG. 9 is a diagrammatic representation of a second exemplary embodiment of a localized pleurodesis chemical delivery system.

The implantable medical device may comprise any suitable size, shape and/or configuration, and may be formed using any suitable biocompatible material. FIG. 9 illustrates one exemplary embodiment of an implantable medical device 900. In this embodiment, the implantable medical device 900 comprises a substantially cylindrical disk 900. The disk 900 is positioned in the pleural space 902 between the thoracic wall 904 and the lung 906. Once in position, the disk 900 elutes or otherwise releases the chemical(s), agent(s) and/or compound(s) that form the pleurodesis. The release rate may be precisely controlled by using any of the various techniques described above, for example, a polymeric diffusion barrier. Also, as stated above, the disk 900 may be formed from a biodegradable material that elutes the chemical(s), agent(s) and/or compound(s) as the disk 900 itself disintegrates or dissolves. Depending upon the material utilized in the construction of the disk 900, a non-biodegradable disk 900 may or may not require removal from the pleural cavity 902 once the pleurodesis is formed. For example, it may be desirable that the disk 900 is a permanent implant that becomes integral with the pleurodesis.

As described in the previous exemplary embodiment, the disk 900 may comprise a radiopaque marker or be formed from a radiopaque material. The radiopaque marker or material allows the disk 900 to be seen under fluoroscopy and then positioned accurately.

In yet another alternate exemplary embodiment, the fluid characteristics of the chemical(s), agent(s) and/or compound(s) may be altered. For example, the chemical(s), agent(s) and/or compound(s) may be made more viscous. With a more viscous chemical agent and/or compound, there would be less chance of the chemical, agent and/or compound moving from the desired location in the pleural space. The chemical(s), agent(s) and/or compound(s) may also comprise radiopaque constituents. Making the chemical(s), agent(s) and/or compounds radiopaque would allow the confirmation of the location of the chemical(s), agent(s) and/or compound(s) with regard to the optimal location of collateral ventilation.

The chemical(s), agent(s) and/or compound(s) as modified above may be utilized in conjunction with standard chemical pleurodesis devices and processes or in conjunction with the exemplary embodiments set forth above.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for treating chronic obstructive pulmonary disease in a lung of a person, the person having a thoracic wall, a parietal membrane, a visceral membrane and a passage which passes through the thoracic wall, the parietal membrane and the visceral membrane into the lung, the parietal membrane being sealed to the visceral membrane surrounding the passage, wherein the method comprises:
   (a) obtaining a ventilation bypass device having a conduit, a flange and a flow-control device, the conduit having an aperture at a distal end to admit gasses from the lung, the flow-control device being connected to a proximal end of the conduit to vent gasses from the conduit, and the flange extending from the conduit spaced from the distal end of the conduit;
   (b) positioning the distal end of the conduit through the passage into the lung of the person;
   (c) securing the flange to the thoracic wall of the person; and
   (d) permitting gasses within the lung of the person to escape through the thoracic wall of the person by entering the aperture, passing through the conduit, and venting through the flow-control device external to the thoracic wall of the person.

2. The method of claim 1, wherein:
   step (a) comprises obtaining a ventilation bypass device having a conduit, a flange and a flow-control device, the conduit having an aperture at a distal end to admit gasses from the lung, the flow-control device being connected to a proximal end of the conduit to vent gasses from the conduit, the flange extending from the conduit spaced from the distal end of the conduit, and a coupling plate having an adhesive coating; and
   step (c) comprises securing the flange to the thoracic wall of the person with the adhesive coating of the coupling plate.

3. The method of claim 1, wherein:
   step (a) comprises obtaining a ventilation bypass device having a conduit, a flange and a flow-control device, the conduit having an aperture at a distal end to admit gasses from the lung, the flow-control device comprising a filter connected to a proximal end of the conduit to vent gasses from the conduit, and the flange extending from the conduit spaced from the distal end of the conduit; and
   step (d) comprises permitting gasses within the lung of the person to escape through the thoracic wall of the person by entering the aperture, passing through the conduit, and venting through the filter external to the thoracic wall of the person.

4. The method of claim 1, wherein:
   step (a) comprises obtaining a ventilation bypass device having a conduit, a flange and a flow-control device, the conduit having an aperture at a distal end to admit gasses from the lung, the flow-control device comprising a valve connected to a proximal end of the conduit to vent gasses from the conduit, and the flange extending from the conduit spaced from the distal end of the conduit; and
   step (d) comprises permitting gasses within the lung of the person to escape through the thoracic wall of the person by entering the aperture in the distal end of the conduit, passing through the conduit, and venting through the valve external to the thoracic wall of the person.

5. The method of claim 1, wherein:
   step (a) comprises obtaining a ventilation bypass device having a conduit, a flange, a trap and a flow-control device, the conduit having an aperture at a distal end to admit gasses from the lung, the flow-control device being connected to a proximal end of the conduit by the trap; and
   wherein the method further comprises (e) storing a discharge from the lung in the trap.

6. The method of claim 1, wherein step (c) comprises:
   (c1) securing a coupling plate to the thoracic wall of the person adjacent the passage; and
   (c2) securing the flange to the coupling plate.

7. The method of claim 1, wherein step (c) comprises:
   (c1) securing a coupling plate to the thoracic wall of the person adjacent the passage with a biocompatible adhesive; and
   (c2) securing the flange to the coupling plate.

8. The method of claim 1, further comprising:
   (e) surgically creating said passage which passes through the thoracic wall, the parietal membrane and the visceral membrane into the lung; and
   (f) sealing the parietal membrane and visceral membrane to one another surrounding the passage.

9. A method for increasing expiratory flow of gasses from a lung of a person, the person having a chest wall, a parietal membrane, a visceral membrane, and a pleural cavity and a passage which passes through the chest wall, the parietal membrane and the visceral membrane into the lung, the passage being sealed from the pleural cavity, wherein the method comprises:
   (a) obtaining a ventilation device having a conduit, a shoulder and a gas-control device, the conduit having a distal aperture to admit gasses from the lung, the gas-control device being attached to a proximal end of the conduit, and the shoulder extending from the conduit spaced from the distal aperture;

(b) positioning the distal aperture of the conduit through the passage into the lung of the person;

(c) attaching the shoulder to the chest wall of the person; and (d) permitting gasses to escape from the lung through the chest wall of the person by entering the distal aperture, passing through the conduit, and venting through the gas-control device external to the person.

10. The method of claim 9, wherein:

step (a) comprises obtaining a ventilation device having a conduit, a shoulder and a gas-control device, the conduit having a distal aperture to admit gasses from the lung, the shoulder having an adhesive, the gas-control device being attached to a proximal end of the conduit, the shoulder extending from the conduit spaced from the distal aperture, and a coupling plate having an adhesive coating; and step (c) comprises attaching the conduit to the person with the adhesive coating of the coupling plate.

11. The method of claim 9, wherein:

(a) obtaining a ventilation device having a conduit, a shoulder and a gas-control device, the conduit having a distal aperture to admit gasses from the lung, the gas-control device comprising a filter connected to a proximal end of the conduit, and the shoulder extending from the conduit spaced from the distal aperture;

step (d) comprises permitting gasses to escape from the lung through the chest wall of the person by entering the distal aperture, passing through the conduit, and venting through the filter external to the person.

12. The method of claim 9, wherein:

step (a) comprises obtaining a ventilation device having a conduit, a shoulder and a gas-control device, the conduit having a distal aperture to admit gasses from the lung, the gas-control device comprising a valve connected to a proximal end of the conduit, and the shoulder extending from the conduit spaced from the distal aperture; and step (d) comprises permitting gasses to escape from the lung through the chest wall of the person by entering the distal aperture, passing through the conduit, and venting through the valve external to the person.

13. The method of claim 9, wherein:

step (a) comprises obtaining a ventilation device having a conduit, a shoulder and a gas-control device, the conduit having a distal aperture to admit gasses from the lung, the gas-control device being attached to a proximal end of the conduit, and the shoulder extending from the conduit spaced from the distal aperture; and wherein the method further comprises (e) storing a discharge from the lung in a trap.

14. The method of claim 9, wherein step (c) comprises:

(c1) attaching a coupling plate to the chest wall of the person adjacent the passage; and (c2) attaching the shoulder to the coupling plate.

15. The method of claim 9, wherein step (c) comprises:

(c1) attaching a coupling plate to the chest wall of the person adjacent the passage with a biocompatible adhesive; and (c2) attaching the shoulder to the coupling plate.

16. The method of claim 9, further comprising:

(e) surgically creating said passage which passes through the chest wall, the parietal membrane and the visceral membrane into the lung; and (f) sealing the passage from the pleural cavity by causing pleurodesis between the parietal membrane and visceral membrane surrounding the passage.

17. A method for reducing hyperinflation of a lung of a person, the person having a chest wall, a parietal membrane, a visceral membrane, and a pleural cavity and a passage which passes through the chest wall, the parietal membrane and the visceral membrane into the lung, the passage being sealed from the pleural cavity, wherein the method comprises:

(a) receiving a gas venting device having a conduit, and a gas-control device, the conduit having a distal opening to admit gasses from the lung, the conduit having a projection extending from the conduit and spaced from the distal opening, the conduit being received through an aperture in a coupling plate such that the coupling plate is positioned between the projection and the distal opening, the gas-control device being connected to a proximal end of the conduit;

(b) inserting the conduit into the passage to position the distal opening within the lung of the person;

(c) contacting the chest wall of the person with the coupling plate;

(d) securing the coupling plate to the chest wall of the person;

(e) permitting gasses to escape from the lung through the chest wall of the person by entering the distal opening, passing through the conduit, and escaping through the gas-control device.

18. The method of claim 17, wherein:

step (a) comprises receiving a gas venting device having a conduit, and a gas-control device, the conduit having a distal opening to admit gasses from the lung, the conduit having a projection extending from the conduit and spaced from the distal opening, the conduit being received through an aperture in a coupling plate such that the coupling plate is positioned between the projection and the distal opening, the gas-control device including a filter connected to a proximal end of the conduit; and step (e) comprises permitting gasses to escape from the lung through the chest wall of the person by entering the distal opening, passing through the conduit, and escaping through the filter.

19. The method of claim 17, wherein:

step (a) comprises receiving a gas venting device having a conduit, and a gas-control device, the conduit having a distal opening to admit gasses from the lung, the conduit having a projection extending from the conduit and spaced from the distal opening, the conduit being received through an aperture in a coupling plate such that the coupling plate is positioned between the projection and the distal opening, the gas-control device including a valve connected to a proximal end of the conduit; and step (e) comprises permitting gasses to escape from the lung through the chest wall of the person by entering the distal opening, passing through the conduit, and escaping through the valve.

20. The method of claim 17, wherein:

step (a) comprises receiving a gas venting device having a conduit, and a gas-control device, the conduit having a distal opening to admit gasses from the lung, the conduit having a projection extending from the conduit and spaced from the distal opening, the conduit being received through an aperture in a coupling plate such that the coupling plate is positioned between the projection and the distal opening, the gas-control device including a filter and a valve connected to a proximal end of the conduit; and step (e) comprises permitting gasses to escape from the lung through the chest wall of the person by entering the distal opening, passing through the conduit, and escaping through the filter and the valve.

21. The method of claim 17, wherein:

step (a) comprises receiving a gas venting device having a conduit, and a gas-control device, the conduit having a distal opening to admit gasses from the lung, the conduit having a projection extending from the conduit and spaced from the distal opening, the conduit being received through an aperture in a coupling plate such that the coupling plate is positioned between the projection and the distal opening, the gas-control device being connected to a proximal end of the conduit, the coupling plate having an adhesive coating; and step (d) comprises securing the coupling plate to the chest wall of the person with the adhesive coating.

22. The method of claim 17, wherein:

step (a) comprises receiving a gas venting device having a conduit, a projection extending from the conduit and spaced from the distal opening, the conduit being received through an aperture in a coupling plate such that the coupling plate is positioned between the projection and the distal opening, a containment vessel, and a gas-control device, the conduit having a distal opening to admit gasses from the lung, the gas-control device being connected by the containment vessel to a proximal end of the conduit; and wherein the method further comprises (f) storing a discharge from the lung in the containment vessel.

23. The method of claim 17, further comprising:

(f) creating said passage which passes through the chest wall, the parietal membrane and the visceral membrane into the lung; and (g) sealing the passage from the pleural cavity by causing pleurodesis between the parietal membrane and visceral membrane surrounding the passage.

24. A method for treating chronic obstructive pulmonary disease of a lung of a person, the person having a thoracic wall, a parietal membrane, a visceral membrane and a passage which passes through the thoracic wall, the parietal membrane and the visceral membrane into the lung, there being pleurodesis between the parietal membrane and visceral membrane surrounding the passage, wherein the method comprises:

(a) receiving a medical device having a tube, a projection and a gas-control device, the tube having a distal opening to admit gasses from the lung, the gas-control device being connected to a proximal end of the tube, and the projection extending from the tube spaced from the distal opening;

(b) inserting the tube through the passage;

(c) positioning the distal opening within the lung of the person;

(d) securing the projection of the tube to the chest wall of the person; and (e) venting gasses from the lung of the person external to the person through the chest wall via the distal opening, the tube, and the gas-control device.

25. The method of claim 24, wherein:

step (a) comprises receiving a medical device having a tube, a projection and a gas-control device, the tube having a distal opening to admit gasses from the lung, the gas-control device being connected to a proximal end of the tube, and the projection extending from the tube spaced from the distal opening, and a coupling plate having an adhesive coating; and step (d) comprises securing the conduit to the chest wall of the person by using the adhesive coating to create a temporary seal between the coupling plate and the chest wall.

26. The method of claim 24, wherein:

step (a) comprises receiving a medical device having a tube, a projection and a gas-control device, the tube having a distal opening to admit gasses from the lung, the gas-control device connected to a proximal end of the tube, the gas-control device including a filter, and the projection extending from the tube spaced from the distal opening;

step (e) comprises venting gasses from the lung of the person external to the person through the chest wall via the distal opening, the tube, and the filter; while (f) filtering said gasses with the filter to capture particulate matter.

27. The method of claim 24, wherein:

step (a) comprises receiving a medical device having a tube, a projection and a gas-control device, the tube having a distal opening to admit gasses from the lung, the gas-control device connected to a proximal end of the tube, the gas-control device including a valve, and the projection extending from the tube spaced from the distal opening;

step (e) comprises venting gasses from the lung of the person external to the person through the chest wall via the distal opening, the tube, and the valve; while (f) maintaining flow of said gases through the tube in one direction with the valve.

28. The method of claim 24, wherein:

step (a) comprises receiving a medical device having a tube, a projection and a gas-control device, the tube having a distal opening to admit gasses from the lung, the gas-control device connected to a proximal end of the tube, the gas-control device including a filter and a valve, and the projection extending from the tube spaced from the distal opening;

step (e) comprises venting gasses from the lung of the person external to the person through the chest wall via the distal opening, the tube, the valve and the filter; while (f) filtering said gasses with the filter to capture particulate matter and maintaining flow of said gases through the tube in one direction with the valve.

29. The method of claim 24, wherein:

step (a) comprises receiving a medical device having a tube, a vessel, a projection and a gas-control device, the tube having a distal opening to admit gasses from the lung, the gas-control device connected by the vessel to a proximal end of the tube, the gas-control device including a filter, and the projection extending from the tube spaced from the distal opening;

step (e) comprises venting gasses from the lung of the person external to the person through the chest wall via the distal opening, the tube, the vessel, and the filter; while (f) filtering the gasses with the filter to capture particulate matter and trapping discharge in the vessel.

30. The method of claim 24, wherein:

step (a) comprises receiving a medical device having a tube, a projection and a gas-control device, the tube having a distal opening to admit gasses from the lung, the gas-control device connected by the vessel to a proximal end of the tube, the gas-control device including a discharge trap, and the projection extending from the tube spaced from the distal opening;

step (e) comprises venting gasses from the lung of the person external to the person through the chest wall via the distal opening, the tube, and the discharge trap; while (f) trapping discharge in the discharge trap.

31. The method of claim 24, wherein step (d) comprises:
(d1) securing a coupling plate to the chest wall of the person adjacent the passage; and
(d2) securing the projection to the coupling plate.

32. The method of claim 24, wherein step (d) comprises:
(d1) adhering a coupling plate to the chest wall of the person adjacent the passage with a biocompatible adhesive; and
(d2) securing the projection to the coupling plate.

33. The method of claim 24, further comprising:
(f) creating said passage which passes through the thoracic wall, the parietal membrane and the visceral membrane into the lung; and
(g) causing pleurodesis between the parietal membrane and visceral membrane surrounding the passage.

34. A method for treating chronic obstructive pulmonary disease by reducing lung volume of a person, the person having a chest wall, a parietal membrane, and a visceral membrane and a passage which passes through the chest wall, the parietal membrane and the visceral membrane into the lung, there being pleurodesis of the visceral membrane and parietal membrane surrounding the passage, wherein the method comprises:
(a) receiving a medical device having a tube, a flange and a gas vent, the tube having a distal opening to admit gasses from the lung, the gas vent being positioned at a proximal end of the tube, and the flange extending from the tube spaced from the distal opening;
(b) inserting the distal opening of the tube through the passage into the lung of the person;
(c) securing the flange to the chest wall of the person; and
(d) permitting gasses to escape from the lung through the chest wall of the person by entering the distal opening, passing through the tube, and escaping through the gas vent external to the person.

35. The method of claim 34, wherein:
step (a) comprises receiving a medical device having a tube, a flange and a gas vent the tube having a distal opening to admit gasses from the lung, the gas vent being positioned at a proximal end of the tube, the flange extending from the tube spaced from the distal opening, and a coupling plate having an adhesive coating; and
step (c) comprises securing the medical device to the chest wall of the person by using the adhesive coating to create a temporary seal between the coupling plate and the chest wall.

36. The method of claim 34, wherein:
step (a) comprises receiving a medical device having a tube, a flange and a gas vent, the tube having a distal opening to admit gasses from the lung, the gas vent being positioned at a proximal end of the tube, the gas vent including a filter, and the flange extending from the tube spaced from the distal opening; and
step (d) comprises permitting gasses to escape from the lung through the chest wall of the person by entering the distal opening, passing through the tube, and escaping through the filter external to the person; while
(e) filtering said gasses with the filter to capture particulate matter.

37. The method of claim 34, wherein:
step (a) comprises receiving a medical device having a tube, a flange and a gas vent, the tube having a distal opening to admit gasses from the lung, the gas vent being positioned at a proximal end of the tube, the gas vent including a valve, and the flange extending from the tube spaced from the distal opening; and
step (d) comprises permitting gasses to escape from the lung through the chest wall of the person by entering the distal opening, passing through the tube, and escaping through a valve external to the person; while
(f) maintaining flow of said gases through the tube in one direction with the valve.

38. The method of claim 34, wherein:
step (a) comprises receiving a medical device having a tube, a flange and a gas vent, the tube having a distal opening to admit gasses from the lung, the gas vent being positioned at a proximal end of the tube, the gas vent including a filter and a valve, and the flange extending from the tube spaced from the distal opening; and
step (d) comprises permitting gasses to escape from the lung through the chest wall of the person by entering the distal opening, passing through the tube, and escaping through the filter and the valve external to the person; while
(e) filtering said gasses with the filter to capture particulate matter and maintaining flow of said gases through the tube in one direction with the valve.

39. The method of claim 34, wherein:
step (a) comprises receiving a medical device having a tube, a flange and a gas vent, the tube having a distal opening to admit gasses from the lung, the gas vent being positioned at a proximal end of the tube, the gas vent including a filter and a container, and the flange extending from the tube spaced from the distal opening; and
step (d) comprises permitting gasses to escape from the lung through the chest wall of the person by entering the distal opening, passing through the tube, and escaping through the container and filter external to the person; while
(e) filtering said gasses with the filter to capture particulate matter and trapping discharge in the container.

40. The method of claim 34, wherein:
step (a) comprises receiving a medical device having a tube, a flange and a gas vent, the tube having a distal opening to admit gasses from the lung, the gas vent being positioned at a proximal end of the tube, the gas vent including a discharge trap, and the flange extending from the tube spaced from the distal opening; and
step (d) comprises permitting gasses to escape from the lung through the chest wall of the person by entering the distal opening, passing through the tube, and escaping through the discharge trap external to the person; while
(e) trapping discharge in the discharge trap.

41. The method of claim 34, wherein step (c) comprises:
(c1) securing a coupling plate to the chest wall of the person adjacent the passage; and
(c2) securing the flange to the coupling plate.

42. The method of claim 34, wherein step (c) comprises:
(c1) securing a coupling plate to the chest wall of the person adjacent the passage with a biocompatible adhesive; and
(c2) securing the flange to the coupling plate.

43. The method of claim 34, further comprising:
(e) surgically creating said passage which passes through the chest wall, the parietal membrane and the visceral membrane into the lung; and (f) creating pleurodesis between the parietal membrane and visceral membrane surrounding the passage.

44. The method of claim 34, wherein:

step (a) comprises receiving a medical device having a tube, a flange and a gas vent, the tube having a distal opening to admit gasses from the lung, the gas vent being positioned at a proximal end of the tube, the gas vent including a discharge trap, and the flange extending from the tube spaced from the distal opening; and step (d) comprises permitting gasses to escape from the lung through the chest wall of the person by entering the distal opening, passing through the tube, and escaping through the discharge trap external to the person; while (e) trapping discharge in the discharge trap; and (f) removing at lease part of the discharge trap after accumulation of discharge.

45. The method of claim 34, wherein:

step (a) comprises receiving a medical device having a tube, a flange and a gas vent, the tube having a distal opening to admit gasses from the lung, the gas vent being positioned at a proximal end of the tube, the gas vent including a discharge trap, the flange extending from the tube spaced from the distal opening; and step (d) comprises permitting gasses to escape from the lung through the chest wall of the person by entering the distal opening, passing through the tube, and escaping through the discharge trap external to the person; while (e) trapping discharge in the discharge trap; and (f) cleaning the discharge trap.

* * * * *